(12) United States Patent
Kabe et al.

(10) Patent No.: US 12,708,782 B2
(45) Date of Patent: Aug. 18, 2026

(54) IMPLANT DELIVERY AND RETRIEVAL SYSTEMS AND METHODS

(71) Applicant: Pacesetter, Inc., Sylmar, CA (US)

(72) Inventors: Arundhati Kabe, Sunnyvale, CA (US); Thomas B. Eby, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 135 days.

(21) Appl. No.: 18/761,220

(22) Filed: Jul. 1, 2024

(65) Prior Publication Data

US 2024/0350811 A1 Oct. 24, 2024

Related U.S. Application Data

(63) Continuation of application No. 16/987,203, filed on Aug. 6, 2020, now Pat. No. 12,029,910, which is a (Continued)

(51) Int. Cl.
*A61N 1/372* (2006.01)
*A61B 17/00* (2006.01)
(Continued)

(52) U.S. Cl.
CPC .... *A61N 1/37205* (2013.01); *A61B 17/00234* (2013.01); *A61N 1/372* (2013.01);
(Continued)

(58) Field of Classification Search
CPC ........... A61B 2017/00353; A61B 2017/00358; A61N 1/362; A61N 1/372; A61N 1/37205;
(Continued)

(56) References Cited

U.S. PATENT DOCUMENTS 7,775,989 B2 8/2010 Nakao
12,029,910 B2 * 7/2024 Kabe .................... A61N 1/3756
(Continued)

OTHER PUBLICATIONS

PCT International Search Report for PCT Counterpart Application No. PCT/US2018/031042 Containing International Search Report, 3 pgs. (Aug. 31, 2018).
(Continued)

*Primary Examiner* — Mohamed G Gabr
(74) *Attorney, Agent, or Firm* — WOMBLE BOND DICKINSON (US) LLP

(57) ABSTRACT

Implementations described and claimed herein provide systems and methods for delivering and retrieving a leadless pacemaker. In one implementation, a leadless pacemaker has a docking end, and the docking end has a docking projection extending from a surface. A docking cap has a body defining a chamber. A retriever has sheaths extending with lumens distally from the chamber. A snare extends between the lumens forming a first snare loop pointing in a first direction and a second snare loop pointing in a second direction with a docking space formed therebetween. The snare is movable between an engaged position and a disengaged position by translating the first snare wire and the second snare wire within the first snare lumen and the second snare lumen. The engaged position includes the first snare wire and the second snare wire tightened around the docking projection within the docking space.

18 Claims, 46 Drawing Sheets

Related U.S. Application Data continuation of application No. 15/588,307, filed on May 5, 2017, now Pat. No. 10,765,872.

(51) Int. Cl.

| | |
|---|---|
| ***A61N 1/05*** | (2006.01) |
| ***A61N 1/362*** | (2006.01) |
| ***A61N 1/375*** | (2006.01) |

(52) U.S. Cl.

CPC .. *A61N 1/3756* (2013.01); *A61B 2017/00292* (2013.01); *A61B 2017/00353* (2013.01); *A61B 2017/00358* (2013.01); *A61N 2001/0578* (2013.01); *A61N 2001/058* (2013.01); *A61N 1/362* (2013.01)

(58) Field of Classification Search

CPC .......... A61N 1/3756; A61N 2001/0578; A61N 2001/058

See application file for complete search history.

(56) References Cited

U.S. PATENT DOCUMENTS

| | | | |
|---|---|---|---|
| 2007/0156197 | A1 | 7/2007 | Root et al. |
| 2011/0270339 | A1 | 11/2011 | Murray, III et al. |
| 2012/0116489 | A1 | 5/2012 | Khairkhahan et al. |
| 2012/0165827 | A1 | 6/2012 | Khairkhahan et al. |
| 2012/0239077 | A1 | 9/2012 | Zaver et al. |
| 2013/0053921 | A1 | 2/2013 | Bonner et al. |
| 2014/0243848 | A1 | 8/2014 | Auricchio et al. |
| 2014/0276908 | A1 | 9/2014 | Raybin et al. |
| 2015/0051609 | A1 | 2/2015 | Schmidt et al. |
| 2015/0051612 | A1 | 2/2015 | Schmidt et al. |
| 2015/0051682 | A1* | 2/2015 | Schmidt ............ A61N 1/37205 607/122 |
| 2015/0201848 | A1 | 7/2015 | Stalker et al. |
| 2015/0335884 | A1 | 11/2015 | Khairkhahan et al. |
| 2016/0067446 | A1 | 3/2016 | Klenk et al. |
| 2016/0228712 | A1 | 8/2016 | Koop |
| 2016/0279423 | A1* | 9/2016 | Kelly ................ A61M 25/0136 |
| 2016/0310723 | A1 | 10/2016 | Eggen et al. |
| 2016/0310747 | A1 | 10/2016 | Grubac et al. |
| 2016/0346002 | A1 | 12/2016 | Avneri et al. |
| 2018/0280058 | A1 | 10/2018 | Meade et al. |

OTHER PUBLICATIONS

PCT Written Opinion for PCT Counterpart Application No. PCT/US2018/031042, 12 pgs. (Aug. 31, 2018).

PCT International Preliminary Report on Patentability for PCT Application No. PCT/US2018/031042, 14 pgs. (Nov. 14, 2019).

* cited by examiner 114
140
136
138
104

114
140
142
136
146
138
148
144
104

114
136
140
142
146
148
138
144
104

300
304
302
306
310
308

300

304
306
302
308
310
202
200
300
304
308
306

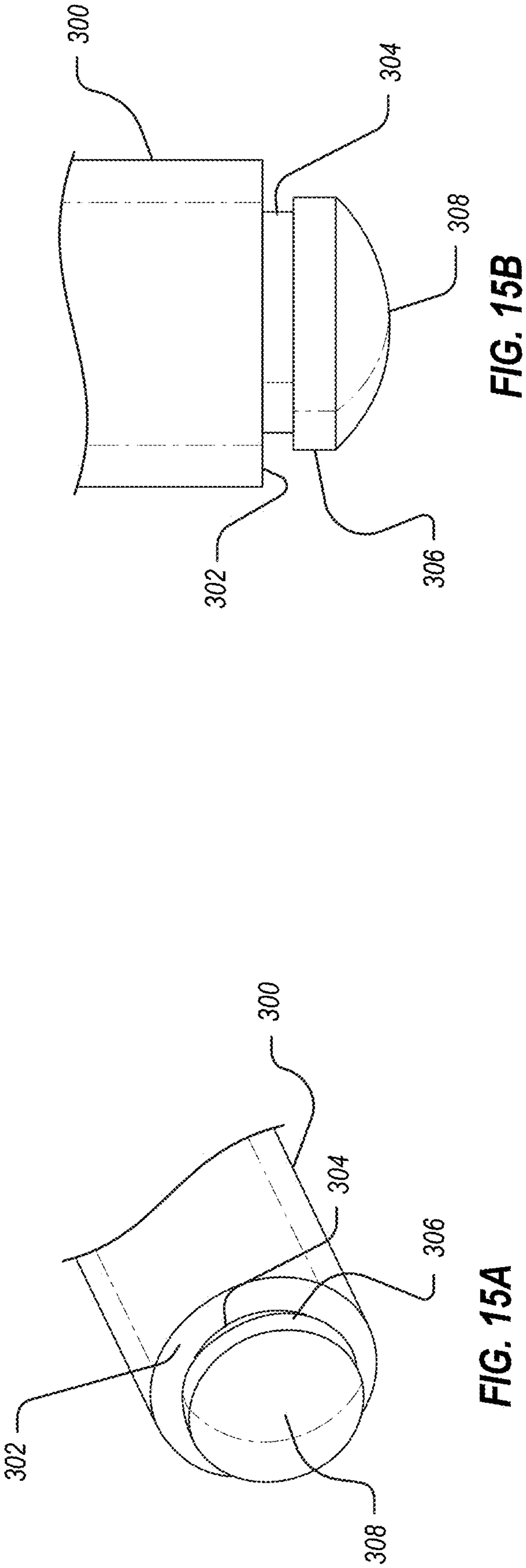
FIG. 15B
FIG. 15A
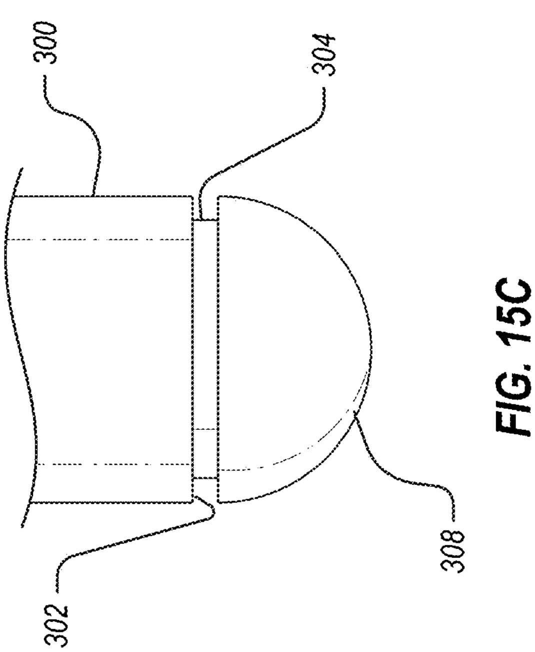
FIG. 15C 114
412
136

138
140
140
138
412
142

136

300
310
306
308
318
302
316
320
328
322
326
324
330

300
302
316
320
328
322
326
324
330
318
308
306
310

IMPLANT DELIVERY AND RETRIEVAL SYSTEMS AND METHODS

This application is a continuation of U.S. patent application Ser. No. 16/987,203, filed Aug. 6, 2020, entitled "IMPLANT DELIVERY AND RETRIEVAL SYSTEMS AND METHODS," which is a continuation of U.S. patent application Ser. No. 15/588,307, filed May 5, 2017, entitled "IMPLANT DELIVERY AND RETRIEVAL SYSTEMS AND METHODS," which are incorporated herein by reference in their entirety.

FIELD

The present disclosure relates to leadless pacemakers and related delivery and retrieval systems and methods. More particularly, the present disclosure relates to systems and methods for loading a leadless pacemaker onto a catheter system for delivery to or retrieval from an implant site.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist. For example, a pulse generator, when located subcutaneously, presents a bulge in the skin that patients can find unsightly, unpleasant, or irritating, and which patients can subconsciously or obsessively manipulate. Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker.

Similar to active fixation implantable leads used with conventional pulse generators, leadless pacemakers are typically fixed to an intracardial implant site by an actively engaging mechanism such as a screw or helical member that threads into the myocardium. Leadless pacemakers are often delivered to an intracardial implant site via a delivery system including a delivery catheter. Conventional delivery catheter systems are typically long (e.g., approximately 42 mm or longer), making navigation of the patient anatomy difficult and increasing a footprint of the system at the implant site.

Some conventional delivery systems are tether based in which attachment of the leadless pacemaker to the delivery catheter is dependent on the tether alignment. Once the tether alignment is lost, which may occur due to system tolerances or anatomical interferences, among other factors, the leadless pacemaker may spontaneously release from the delivery catheter. Such a spontaneous release may cause embolism, a need to retrieve the leadless pacemaker, and/or other patient risks. Retrieval may be performed by removing the delivery catheter and introducing a retrieval catheter to remove the leadless pacemaker. The delivery catheter system is generally different in structure and operation from the retrieval catheter system, which increases procedure time, complexity, and cost. If retrieval cannot be performed using a retrieval catheter system, the leadless pacemaker is typically retrieved through surgery, further complicating the procedure. Moreover, implanting a second leadless pacemaker into a patient often requires the use of a second catheter delivery system, as many conventional catheter systems fail to accommodate bed-side loading of leadless pacemakers onto a previously used catheter system. Instead, many conventional catheter systems are preloaded during manufacturing. It is with these observations in mind, among others, that the presently disclosed technology was conceived and developed.

SUMMARY OF THE DISCLOSURE

Implementations described and claimed herein address the foregoing observations by providing systems and methods for delivering and retrieving a leadless pacemaker. In one implementation, a leadless pacemaker has a docking end, and the docking end has a docking projection extending from a surface. A docking cap has a body defining a chamber. The docking cap has a proximal opening into the chamber, and the proximal opening is coaxial with a longitudinal axis of a lumen of a catheter. A retriever has a first sheath and a second sheath extending distally from the chamber. The first sheath has a first lumen, and the second sheath has a second lumen. A snare includes a first snare wire and a second snare wire. The first snare wire extends from the first snare lumen into the second snare lumen forming a first snare loop pointing in a first direction, and the second snare wire extends from the first snare lumen into the second snare lumen forming a second snare loop pointing in a second direction different from the first direction. The first snare loop and the second snare loop form a docking space. The snare is movable between an engaged position and a disengaged position by translating the first snare wire and the second snare wire within the first snare lumen and the second snare lumen. The engaged position includes the first snare wire and the second snare wire tightened around the docking projection within the docking space.

In another implementation, a docking cap has a body defining a chamber. A retriever has a first sheath and a second sheath extending distally from the chamber. The first sheath is disposed at a position radially opposite to the second sheath relative to a central axis. The first sheath has a first lumen, and the second sheath has a second lumen. A snare includes a first snare wire and a second snare wire. The first snare wire extends from the first snare lumen into the second snare lumen forming a first snare loop having a first peak at the central axis. The second snare wire extends from the first snare lumen into the second snare lumen forming a second snare loop having a second peak at the central axis. The snare is movable between an engaged position and a disengaged position by translating the first snare wire and the second snare wire within the first snare lumen and the second snare lumen. The translation of the first snare wire and the second snare wire move the first peak radially inwards toward the second peak to the engaged position and radially outwards away from the second peak to the disengaged position.

In yet another implementation, a docking space is disposed relative to a docking projection extending from a surface of a body of a leadless pacemaker. The docking space is formed by a first snare loop pointing in a first direction and a second direction different than the first direction. The first snare loop is formed from a first snare wire extending from a first snare lumen of a first sheath into a second snare lumen of a second sheath. The second snare loop is formed from a second snare wire extending from the first snare lumen of the first sheath into the second snare lumen of the second sheath. The first snare loop and the second snare loop are advanced over the leadless pacemaker until the docking projection is disposed in the docking space. A size of the docking space is decreased by retracting the first snare wire and the second snare wire into the first snare lumen and the second snare lumen until the first snare wire and the second snare wire tighten around the docking projection. The first sheath and the second sheath are retracted into a lumen of a catheter until the docking projection is positioned within a chamber of a docking cap.

In still another implementation, a leadless pacemaker has a docking end, and the docking end having a docking projection extending from a surface. A docking cap has a body defining a chamber. The docking cap has a proximal opening into the chamber. The proximal opening is coaxial with a longitudinal axis of a lumen of a catheter. A retriever has a flexible grasper with a first arm disposed opposite a second arm. Each of the first arm and the second arm form a hinge biased radially outwards from the longitudinal axis. The docking cap locks the first arm and the second arm on the docking projection when the body is sheathed over the retriever until the flexible grasper is disposed within the chamber.

In another implementation, a flexible grasper is disposed relative to a docking projection extending from a surface of a body of a leadless pacemaker. The flexible grasper has a first arm disposed opposite a second arm. Each of the first arm and the second arm forms a hinge biased radially outwards from a longitudinal axis. The docking projection is posited between the first arm and the second arm. A body of a docking cap is sheathed over the flexible grasper. The docking cap locks the first arm and the second arm on the docking projection by one or more cap surfaces disposed relative to the chamber displacing the first arm and the second arm radially inwards holding the first arm and the second arm in compression around the docking projection.

In yet another implementation, a leadless pacemaker has a docking end, and the docking end has an opening defined in a surface. A retriever has a first arm disposed opposite a second arm around a central lumen. Each of the first arm and the second arm forms a hinge biased radially inwards towards the central lumen. The first arm and the second arm are displaceable radially outwards by a mandrel translated through the central lumen towards the docking end. The radial outward displacement of the first arm and the second arm engages the surface of the docking end within the opening.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 15A-15C show examples of the docking projection with a round surface.

DETAILED DESCRIPTION

Aspects of the present disclosure involve systems and methods for delivering and retrieving a leadless biostimulator, such as a leadless pacemaker. Generally, the leadless pacemaker is delivered and retrieved from an implant location in a patient using a catheter system. The presently disclosed systems and methods thus facilitate repeated implantation and/or retrieval of leadless pacemakers via a single catheter delivery and retrieval system, thereby reducing waste and the costs associated therewith. Additionally, the systems and methods described herein permit a single catheter system to deliver and retrieve different leadless pacemakers having varying configurations further reducing the operation burden of stocking multiple systems applicable to the various configurations.

In one aspect, the catheter system includes a retriever in the form of a grasper, a snare, and/or the like, releasably engagable to a docking end of the leadless pacemaker to provide torque transmission to the leadless pacemaker during deployment, as well as providing the engagement, delivery, detachment, and/or retrieval of the leadless pacemaker. The retriever reduces the risk of spontaneous or otherwise undesired release of the leadless pacemaker from the catheter during delivery or retrieval. Moreover, the retriever provides reliable detachment independent of a relative position of a dual-tether system and isolates rotation forces of the leadless pacemaker from the catheter system, which may otherwise cause binding and/or torque-wind in a dual-tether system. Tool-less, bed-side loading is facilitated with the presently disclosed technology, permitting the deployment of multiple leadless pacemakers into the patient anatomy with reduced tissue trauma to the patient anatomy during deployment due to the radial opening of the retriever.

The systems and methods described herein generally relate to a loading tool having a retriever for releasably engaging a docking projection of a medical implant, as well as to methods of delivering and retrieving the same. While the present disclosure is discussed with reference to leadless cardiac pacemakers and torque as a loading technique, it will be appreciated that the presently disclosed technology is applicable to other biostimulators and/or medical implant systems and methods as well as loading techniques.

Figure 1:
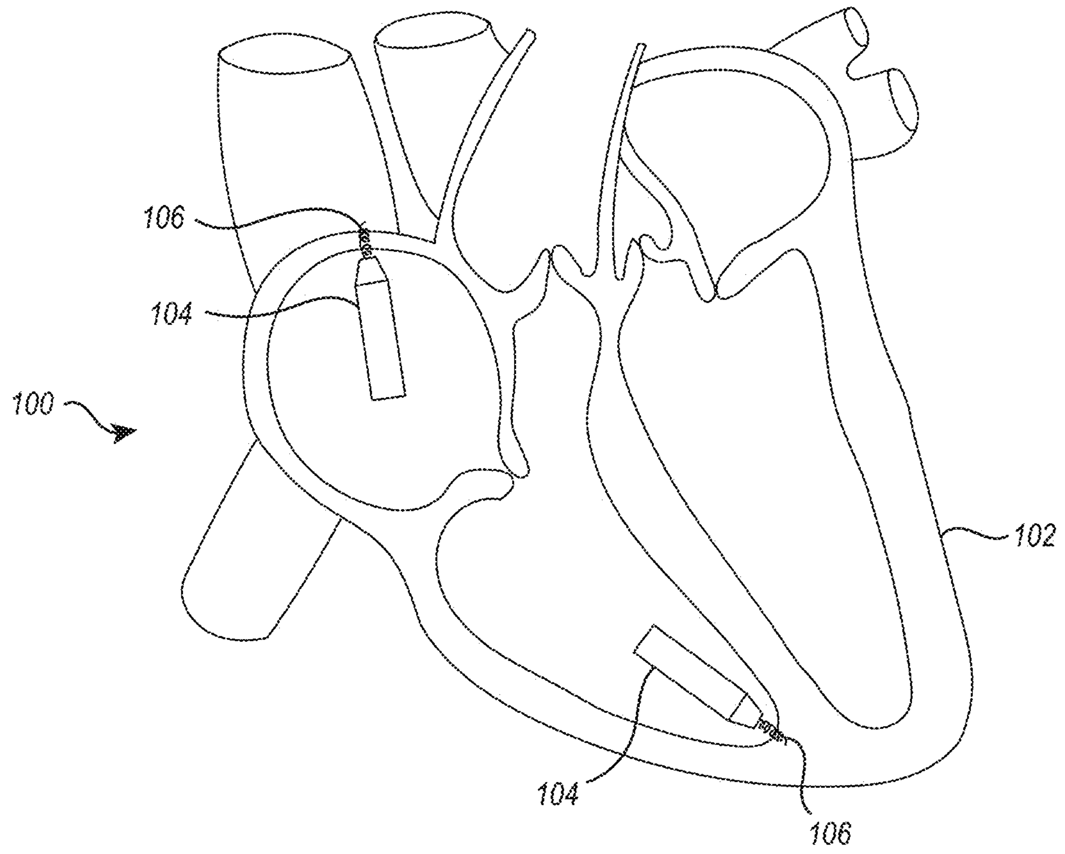
FIG. 1 is a diagrammatic medial-lateral cross-section of a patient heart illustration an example cardiac pacing system having one or more leadless pacemakers.

To begin a detailed description of an example cardiac pacing system 100 having one or more leadless pacemakers 104, reference is made to FIG. 1. The leadless pacemakers 104 may each be configured for temporary leadless pacing of a patient heart 102. In one implementation, each of the leadless pacemakers 104 is configured for placement on or attachment to the inside or outside of a cardiac chamber, such as the right atrium and/or right ventricle, of the patient heart 102. The leadless pacemakers 104 may be attached to cardiac tissue of the patient heart 102, for example, via a helical anchor 106 that is threaded through the myocardium. It will be appreciated, however, that other primary fixation mechanisms, as well as secondary fixation mechanisms in some cases, may be used to attach the leadless pacemaker 104 to tissue or otherwise restrict movement of the leadless pacemaker 104 during implantation.

Figure 2:
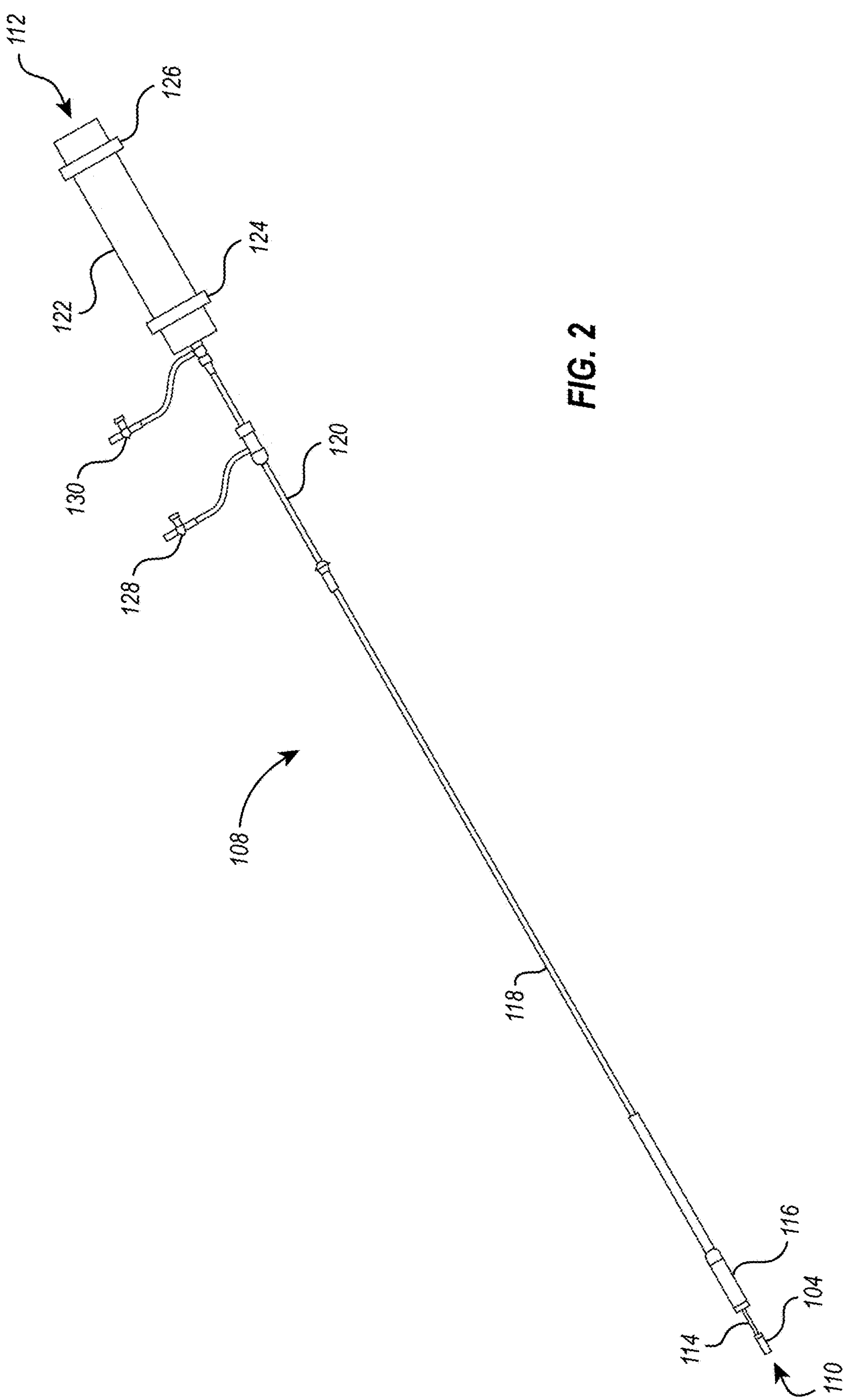
FIG. 2 shows an example catheter system for delivering and/or retrieving a leadless pacemaker.

The leadless pacemakers 104 are delivered to and/or retrieved from the patient heart 102 using a catheter system 108, as shown in FIG. 2. Generally, the catheter system 108 releasably engages the leadless pacemaker 104 for intravenous advancement into the patient heart 102. The catheter system 108 engages the leadless pacemaker 104 in such a manner as to facilitate fixation to cardiac tissue, for example, using the helical anchor 106. As described herein, where the fixation mechanism engages the cardiac tissue through rotation, such as with the helical anchor 106, the catheter system 108 is adapted to provide torque transmission to the leadless pacemaker 104. Stated differently, the catheter system 108 engages features of the leadless pacemaker 104 to apply torque to the leadless pacemaker 104 to screw the helical anchor 106 into cardiac tissue.

The catheter system 108 engages the leadless pacemaker 104 at a distal end 110 and includes a handle at a proximal end 112 for directing the delivery and/or retrieval of the leadless pacemaker 104. In one implementation, the catheter system 108 includes a torque shaft 114, a sleeve 116, and an introducer sheath 120. The catheter system 108 may also include a steerable catheter 116 for deflecting the catheter system 108 and/or one or more flush ports 128 and 130 for flushing saline or other fluids through the catheter system 118.

The torque shaft 114 provides torque transmission to the leadless pacemaker 104 from the steerable catheter 118 and otherwise directs movement of the leadless pacemaker 104 as controlled by one or more steering knobs (e.g., a first steering knob 124 and a second steering knob 126) disposed on a handle body 122. The introducer sheath 120 can be advanced distally over the steerable catheter 118 to provide additional steering and support for the steerable catheter 118 during delivery and/or retrieval and to surround the leadless pacemaker 104 as it is introduced through a trocar or introducer into the patient anatomy. Similarly, the sleeve 116 is movable along the steerable catheter 118 and may be displaced distally over the leadless pacemaker 104 to cover the torque shaft 114, the leadless pacemaker 104, and the helical anchor 106 to protect patient tissue and anatomy during delivery and/or retrieval.

Figure 3:
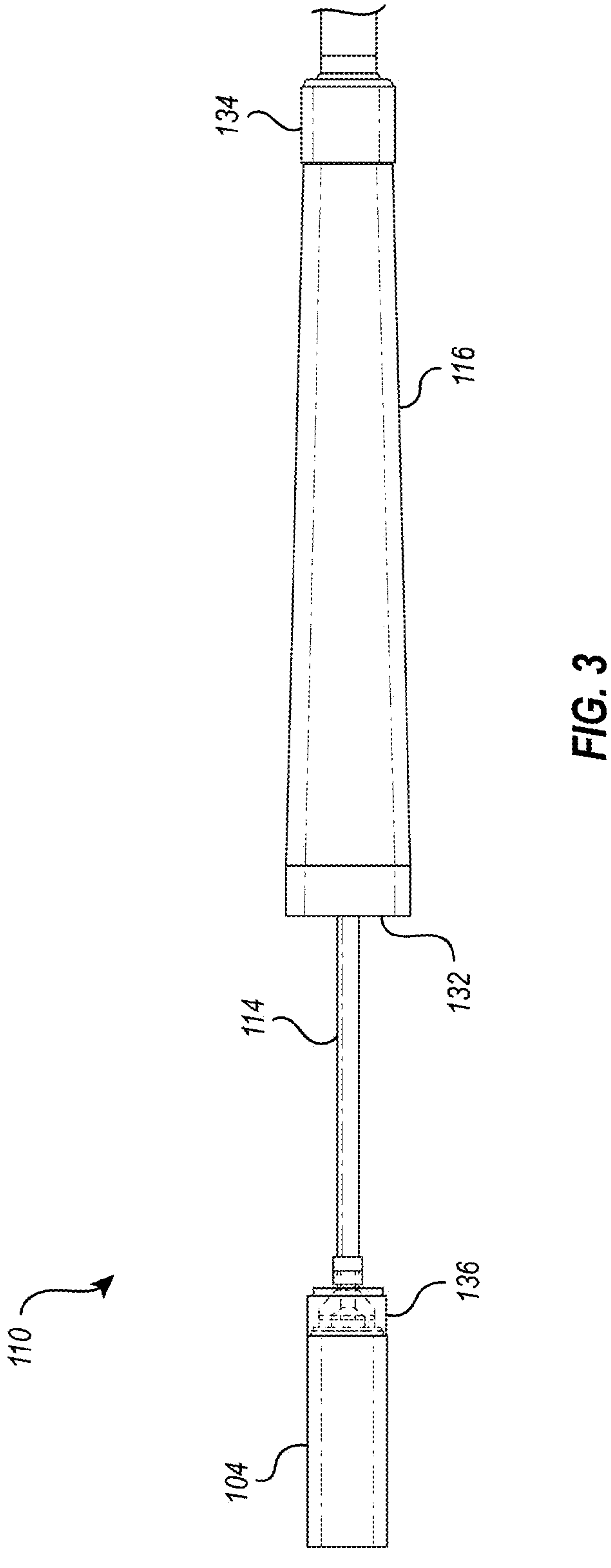
FIG. 3 is a detailed view of a distal end of the catheter system.

Turning to FIG. 3, a detailed view of the distal end 110 of the catheter system 118 is shown. In one implementation, the steerable catheter 118 extends through a sleeve cap 134 into the sleeve 116 where it is engaged to the torque shaft 114. The sleeve 116 may be displaceable over the torque shaft 114 and leadless pacemaker 104 such that the leadless pacemaker 104 is within the sleeve 116 proximal to a distal edge 132 of the sleeve 116. The sleeve 116 may also be steerable.

Figures 4A, 4B, 4C:
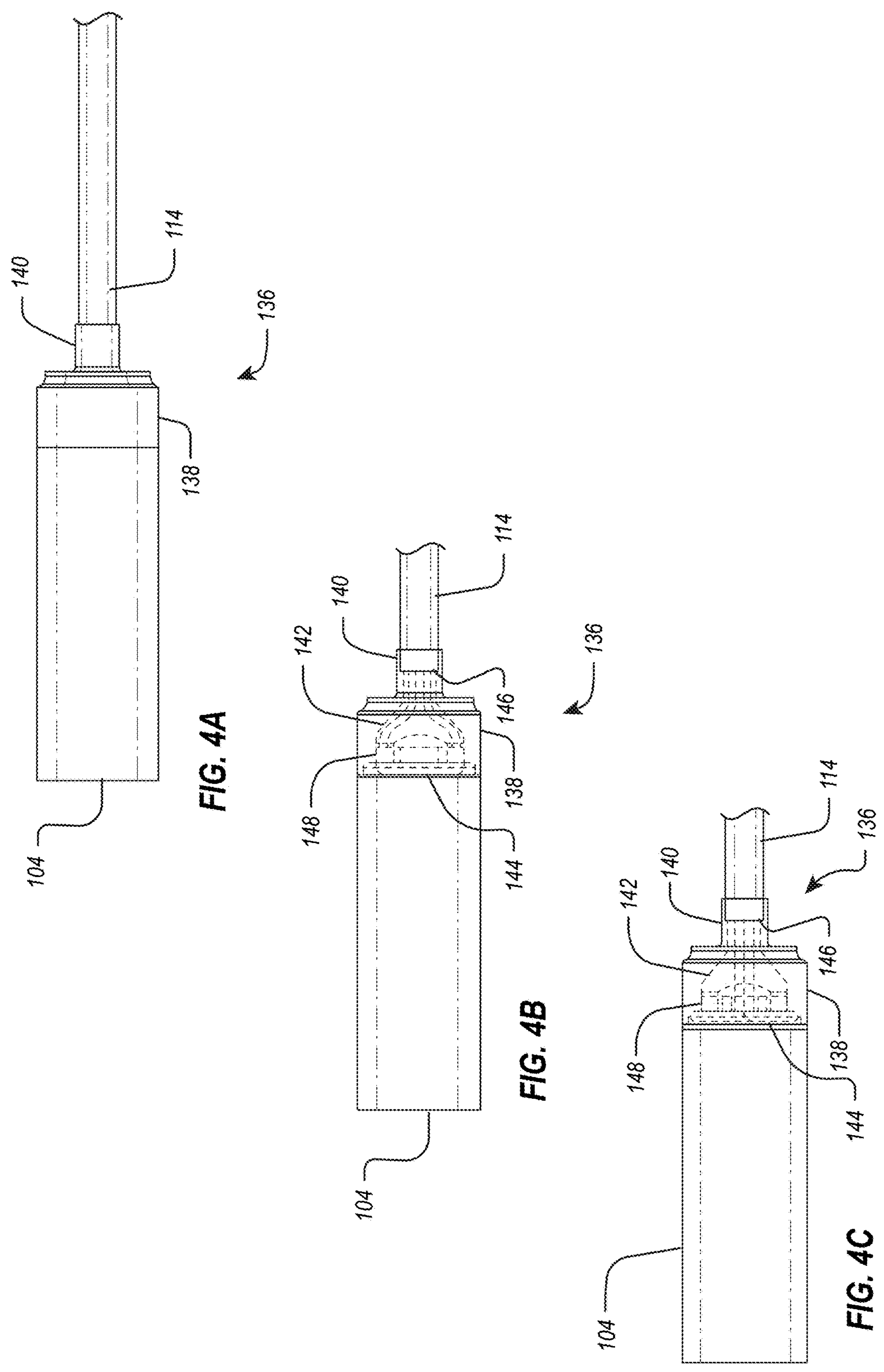
FIGS. 4A-4C each show a retriever in a docked position with a leadless pacemaker with FIGS. 4B and 4C being side and top views, respectively, and showing a docking cap transparent.

In one implementation, a distal end of the torque shaft 114 is engaged to a docking cap 136, which is configured to releasably engage the leadless pacemaker 104. The torque shaft 114 and the docking cap 136 each deliver torque to the leadless pacemaker 104 during delivery and/or retrieval. FIGS. 4A-4C illustrate the catheter system 108 in a docked or engaged position with the docking cap 136 sheathed over a docking end of the leadless pacemaker 104. In one implementation, the docking cap 136 includes a body 138 and a receiving portion 140 configured to engage a distal end 146 of the torque shaft 114. The distal end 146 of the torque shaft 114 may remain rigidly attached to the receiving portion 140 during use.

The body 138 of the docking cap 136 defines a chamber 142. As can be understood from FIGS. 4B-4C, a docking projection 148 extending from the docking end of the leadless pacemaker 104 is disposed within the chamber 142 in the docked position. A retriever 144 is displaceable within a lumen of the torque shaft 114 and configured to releasably engage the docking projection 148. More particularly, the retriever 144 is extendable through the body 138 of the docking cap 136 for placement relative to the docking projection 148, and the body 138 of the docking cap 136 is sheathed over the docking projection 148 causing the retriever 144 to capture the docking projection 148 within the chamber 142.

Figure 5:
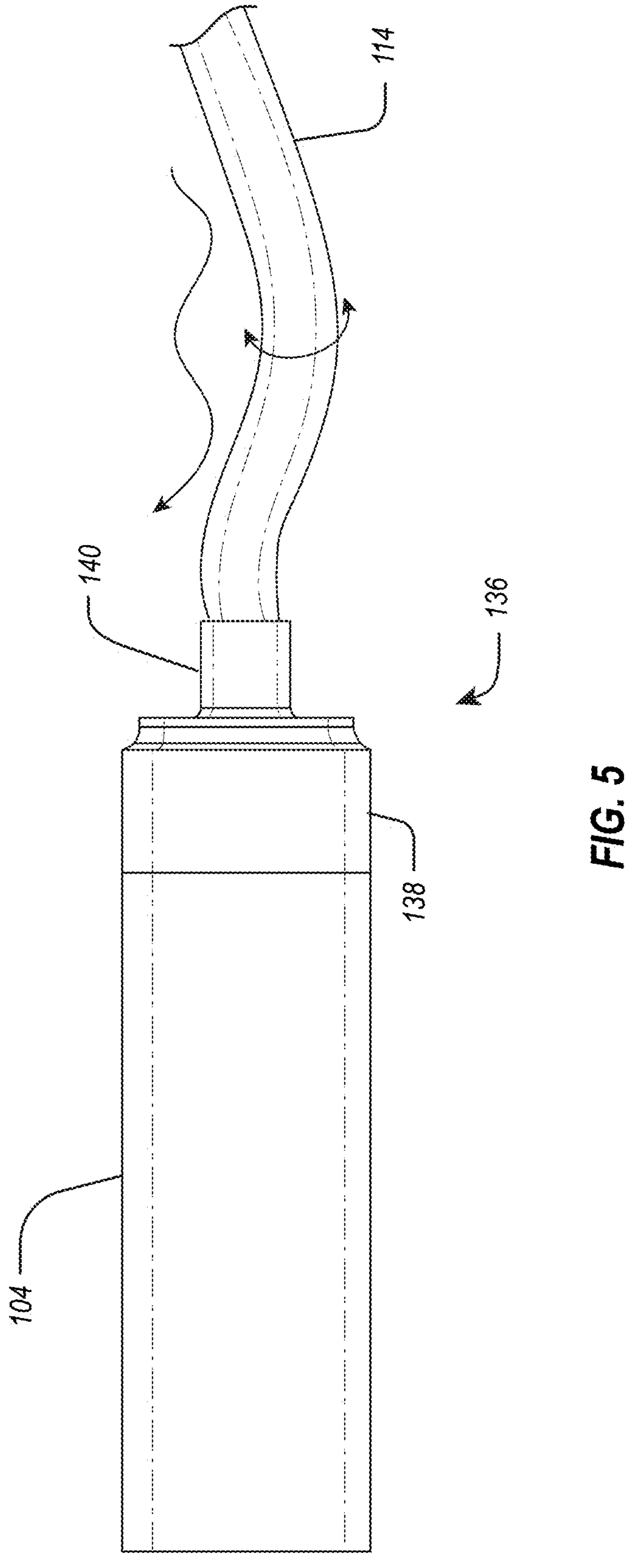
FIG. 5 depicts example movement of a flexible element, such as a torque shaft or a catheter.

In the docked position, the catheter system 108 provides torque transmission to the leadless pacemaker 104. FIG. 5 illustrates that during a test mode or to reposition or otherwise manipulate the leadless pacemaker 104 during deployment, the torque shaft 114 is torqueable and adjustable with a freedom of movement in a plurality of directions. The torque shaft 114 may be flexible and/or made from a variety of materials. For example, the torque shaft 114 may be made from a polymer, metal, and/or the like. The torque shaft 114 may be made with a catheter lamination construction, formed as a hollow helical cable, and/or in other configurations for torque transmission and steering. In one implementation, the torque shaft 114 and/or the steerable catheter 118 is a hypo tube. In other implementations, the torque shaft 114 and/or the steerable catheter 118 includes a cable tube, a laser cut tube, an extrusion, a wire, a wire cable, and/or the like for increased flexibility.

Figure 6:
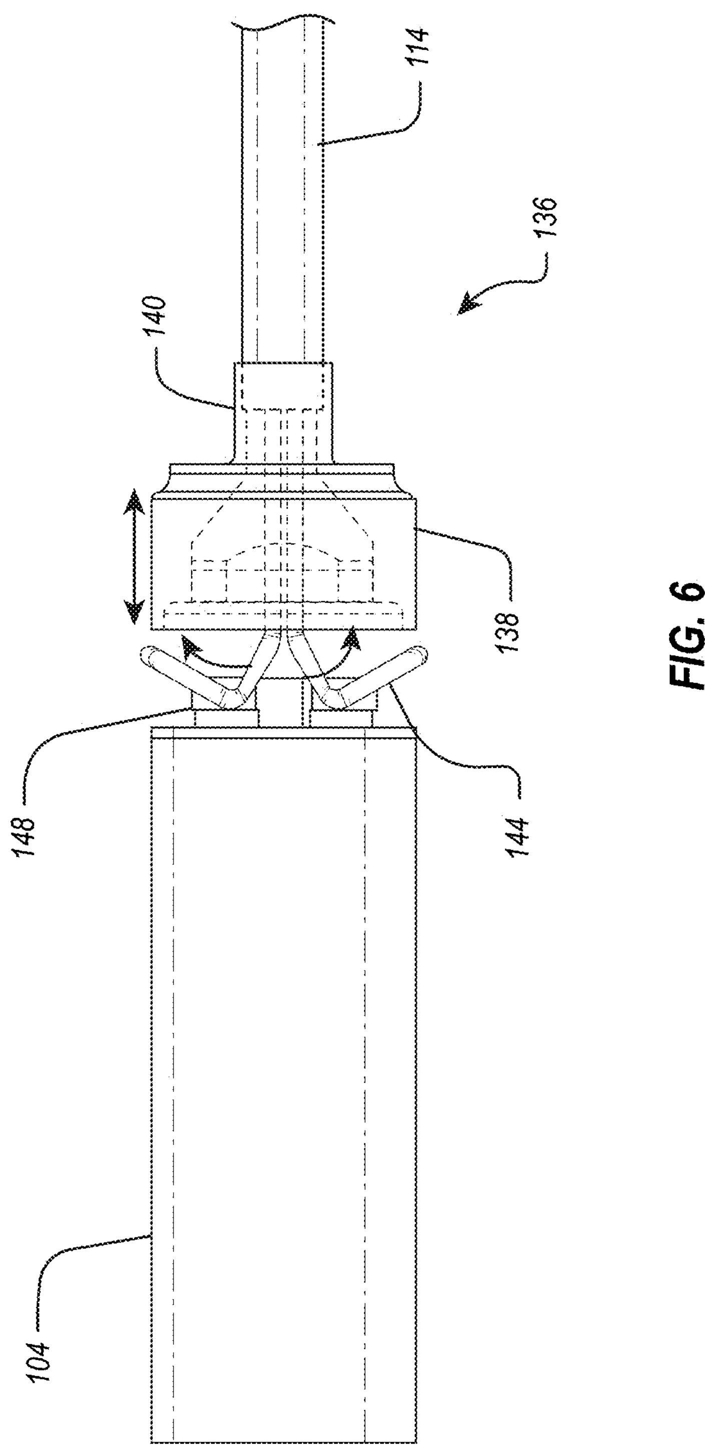
FIGS. 6 and 7 illustrate a side view and a perspective view of the retriever releasing or capturing the leadless pacemaker.
Figure 7:
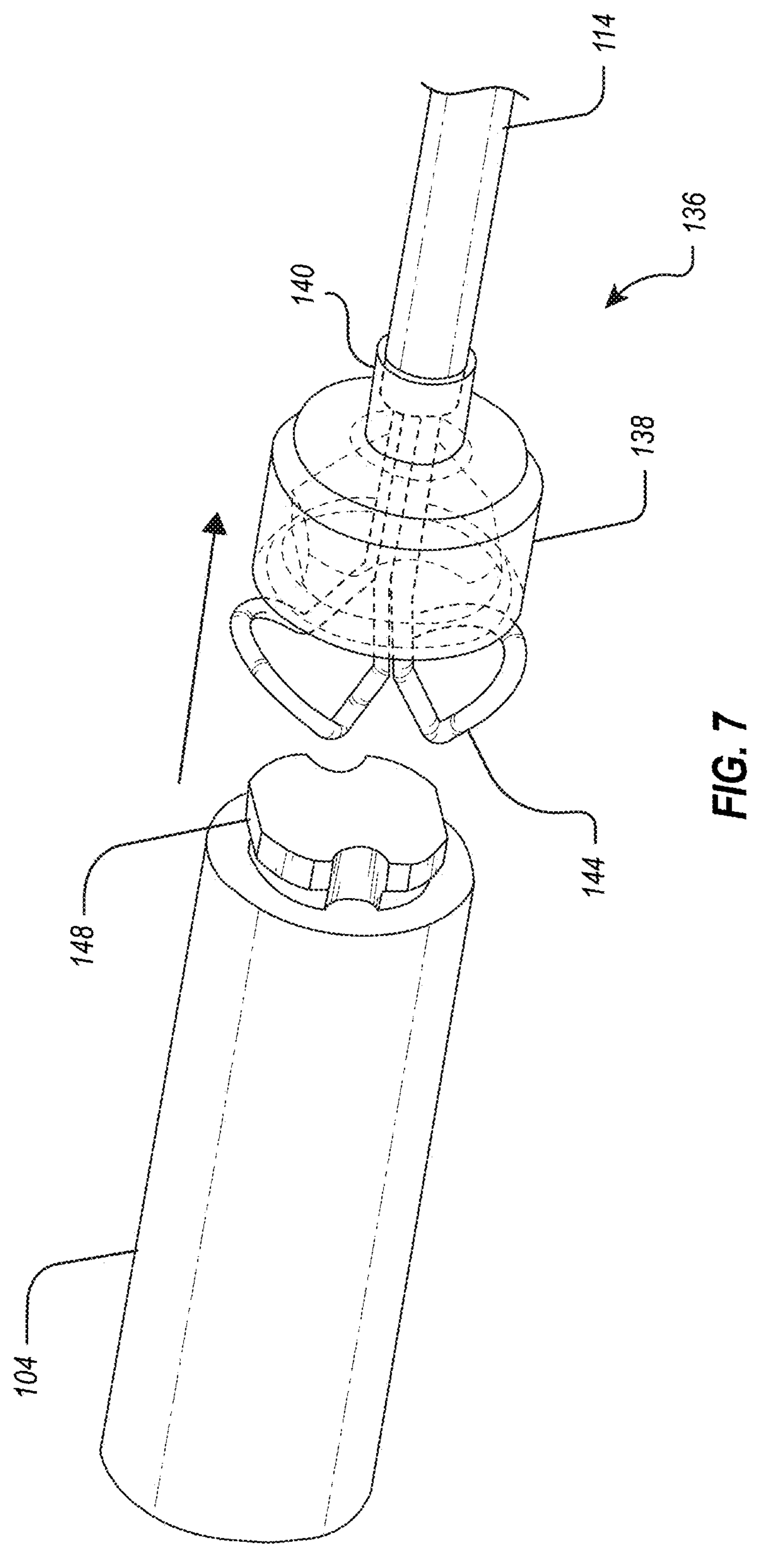

As can be understood from FIG. 6, the docking cap 136 is displaceable over the retriever 144 to cause the retriever 144 to move between an engaged position where the retriever 144 is engaged to the docking projection 148 within the chamber 142 and the catheter system 108 is docked to the leadless pacemaker 104 and a disengaged position where the retriever 144 is disposed in its natural state outside the chamber 142 and disengaged from the docking projection 148. As shown in FIGS. 6 and 7, in one implementation, the docking cap 136 is retracting proximally causing the retriever 144 to open radially to its natural state, thereby releasing the docking projection 148 and disengaging the leadless pacemaker 104. To recapture the leadless pacemaker for retrieval, repositioning, and/or the like, the retriever 144 is positioned relative to the docking projection 148 and the docking cap 136 is sheathed over the retriever 144 causing the retriever 144 to close radially over the docking projection 148 within the chamber 142.

In one implementation, the retriever 144 is a flexible grasper with a first arm disposed opposite a second arm that each form a hinge biased radially outwards from a longitudinal axis of the retriever 144. Stated differently, the retriever 144 is biased open in its natural state in free space, as shown in FIGS. 6 and 7. In one implementation, the natural state of the retriever 144 provides an opening defined by the arms with an inner diameter that is larger than a diameter of the docking projection 148 and in some examples a body of the leadless pacemaker 104. The retriever 144 in the form of a flexible grasper may be made from a variety of elastic or otherwise flexible materials, including, but not limited to, Nitinol or other memory wire, cable, tubing, and/or the like.

As can be understood from FIGS. 4A-7, the docking cap 136 translates axially over the retriever 144 to move the catheter system 108 between the docked and released positions. In one implementation, the body 138 of the docking cap 136 includes one or more cap surfaces disposed relative to the chamber 142. The cap surfaces displace the arms of the retriever 144 radially inwards to hold the arms in compression around the docking projection 148. As such, the docking cap 136 and the docking end of the leadless pacemaker 104 are configured such that the retriever 144 remains locked on the docking projection 148 when the docking cap 136 is sheathed over the retriever 144. This docked position facilitates delivery through the patient anatomy to a target location in the patient heart 102 for implantation. Once implanted, the docking cap 136 is retracted proximally, allowing the arms of the retriever 144 to open radially outwards to the natural state and thereby releasing the docking projection 148. The catheter system 108 is then removed from the patient. The docking projection 148 may be recaptured for retrieval or repositioning by sheathing the docking cap 136 over the retriever 144. During release and capture, tugging on or trauma to patient tissue is reduced or eliminated with the radial movement of the arms of the retriever 144 between the engaged and disengaged positions.

Figure 8:
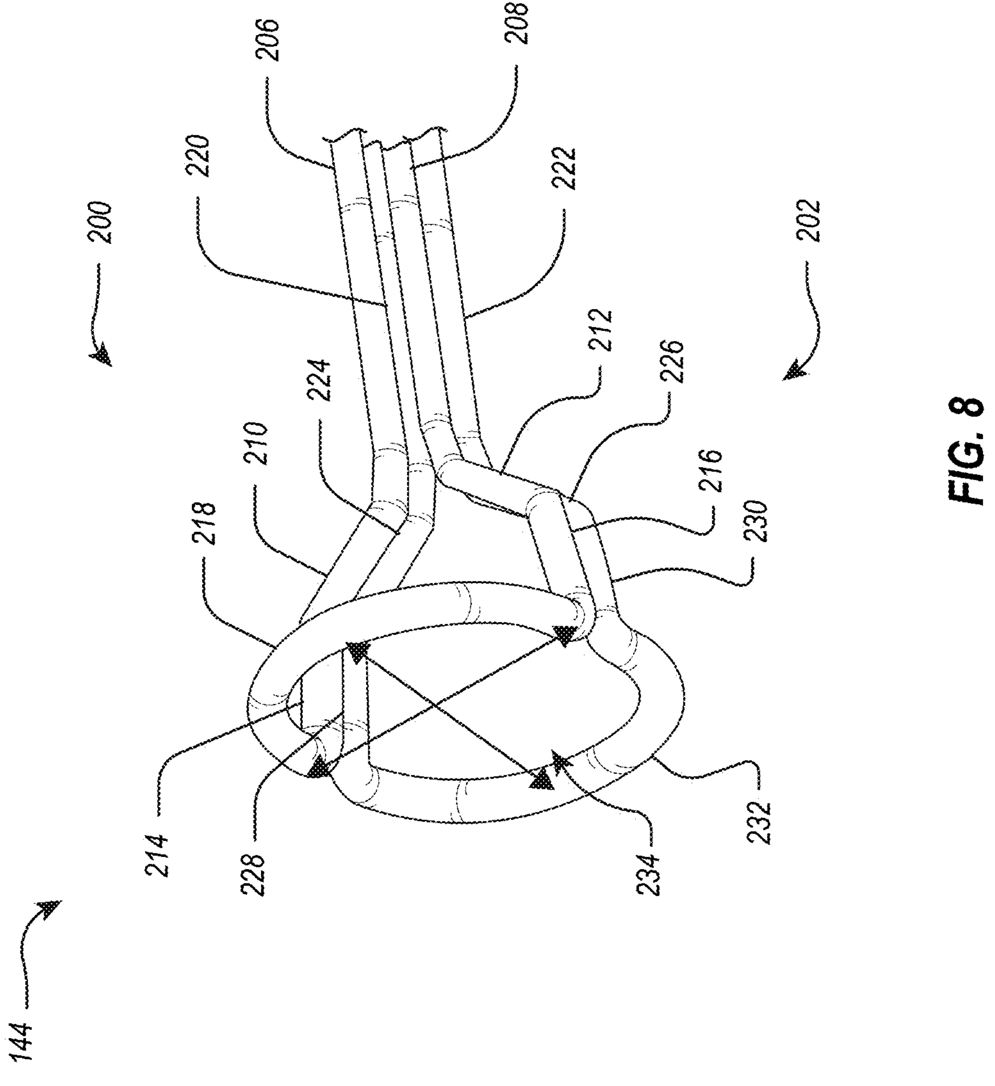
FIG. 8 shows the retriever in the form of an example of a flexible grasper adapted to open radially to release the leadless pacemaker.
Figure 9:
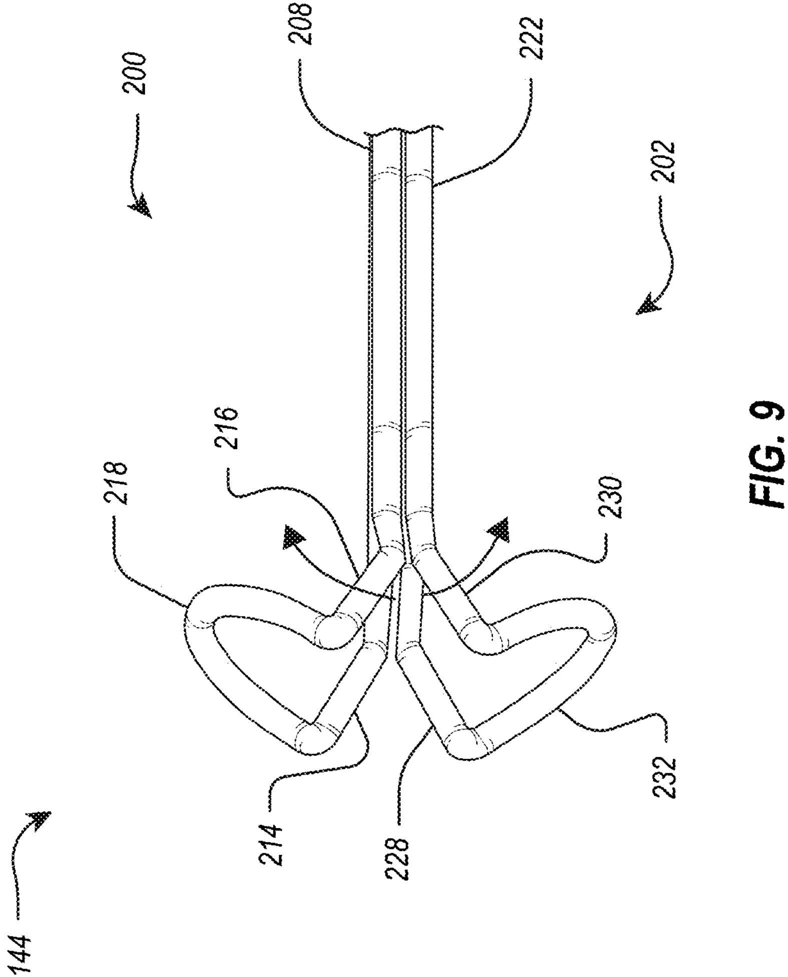
FIG. 9 shows the retriever in the form of another example of a flexible grasper adapted to hinge laterally to release the leadless pacemaker.

FIGS. 8 and 9 show examples of the retriever 144 in the form of a flexible grasper with a first arm 200 and a second arm 202 each forming a flexible loop attached to one or more mandrels extending through a lumen of the torque shaft 114. In one implementation, the first arm 200 includes one or more elongated bodies (e.g., a first elongated body 206 and a second elongated body 208). The first elongated body 206 may extend parallel to the second elongated body 208 within a first plane with a gap formed therebetween. A set of tapering portions connect the one or more elongated bodies to a set of grasping portions. In one implementation, a first grasping portion 214 is connected to the first elongated body 206 with a first tapering portion 210 on the first plane, and a second grasping portion 216 is connected to the second elongated body 208 with a second tapering portion 212 on the first plane. The first grasping portion 214 is generally parallel to the second grasping portion 216 and the first and second elongated bodies 206 and 208. A distance between the first and second grasping portions 214 and 216 is larger than a distance between the first and second elongated bodies 206 and 208, such that the first and second tapering portions 210 and 212 extend inwardly from the first and second grasping portions 214 and 216 to the first and second elongated bodies 206 and 208. The flexible loop of the first arm 200 is formed by a first looped portion 218 extending along a curve between the first and second grasping portions 214 and 216.

The second arm 202 may mirror the first arm 200. In one implementation, the second arm 202 includes one or more elongated bodies (e.g., a third elongated body 220 and a fourth elongated body 222). The third elongated body 220 may extend parallel to the fourth elongated body 222 within a second plane with a gap formed therebetween. The second plane is parallel to the first plane. A second set of tapering portions connect the one or more elongated bodies to a second set of grasping portions. In one implementation, a third grasping portion 228 is connected to the third elongated body 220 with a third tapering portion 224 on the second plane, and a fourth grasping portion 230 is connected to the fourth elongated body 222 with a fourth tapering portion 226 on the second plane. The third grasping portion 228 is generally parallel to the fourth grasping portion 230 and the third and fourth elongated bodies 220 and 222. A distance between the third and fourth grasping portions 228 and 230 is larger than a distance between the third and fourth elongated bodies 220 and 222, such that the third and fourth tapering portions 224 and 226 extend inwardly from the third and fourth grasping portions 228 and 230 to the third and fourth elongated bodies 220 and 222. The flexible loop of the second arm 202 is formed by a second looped portion 232 extending along a curve between the third and fourth grasping portions 228 and 230.

As can be understood from FIGS. 8 and 9, which show the docked position and the natural state of the retriever 144, respectively, in one implementation, the first arm 200 and the second arm 202 each form a hinge biased radially outwards from a longitudinal axis of the retriever 144. When the retriever 144 is in the docked position, the first set of grasping portions 214 and 216 are positioned adjacent the second set of grasping portions 228 and 230 within the first and second planes. In the docked position, the first and second looped portions 218 and 232 extend in opposite directions, forming a ring defining a docking space 234 therebetween. The docking space 234 may be sized and shaped to match a size and shape of the docking projection 148 with the first arm 200 and second arm 202 adapted to matingly engage the features of the docking projection 148 as described herein.

In moving to the natural state, the first arm 200 and the second arm 202 hinge radially outward from the longitudinal axis such that the first set of grasping portions 214 and 216 are positioned at an angle relative to the second set of grasping portions 228 and 230 with each at an angle relative to the first and second planes. In one implementation, when the docking cap 136 is retracted proximally, the ring formed by the first and second looped portions 218 and 232 opens radially outwards to a larger diameter, thus releasing the docking projection 148.

Figure 10B:
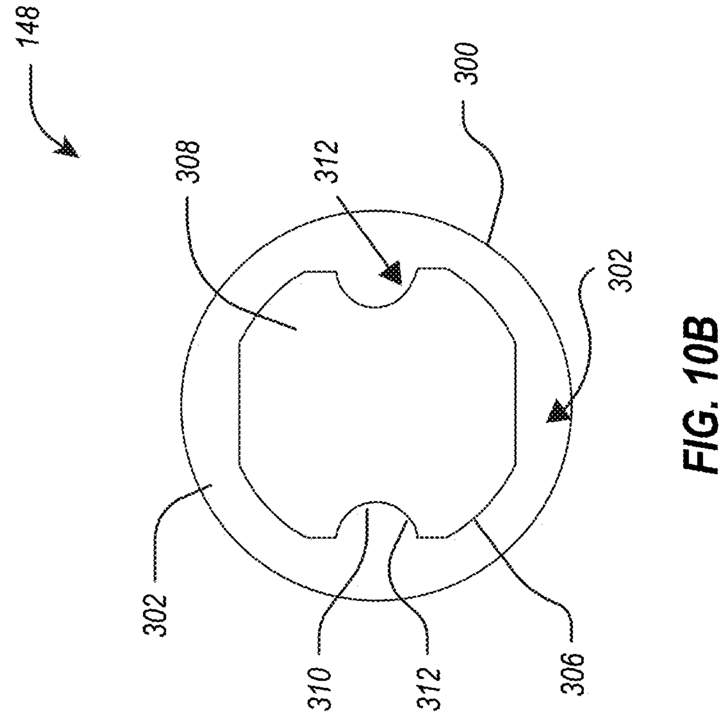
FIGS. 10A and 10B depict a perspective view and a back view, respectively, of an example docking end of a leadless pacemaker.
Figure 10A:
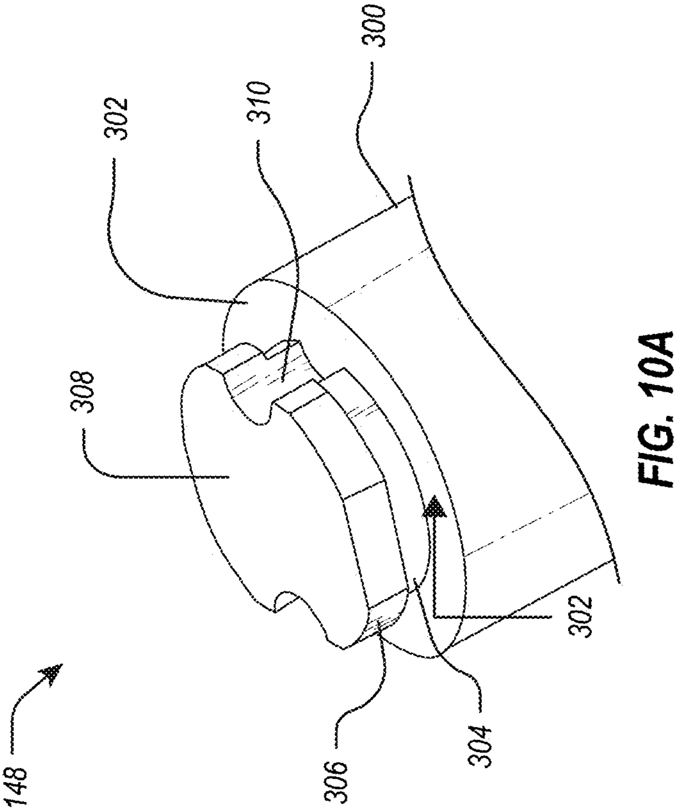

Turning to FIGS. 10A-10B, the docking projection 148 may include features adapted to matingly engage with the first arm 200 and the second arm 202 and the docking cap 136 to facilitate capture by the retriever 144 and to provide torque transmission. In one implementation, the leadless pacemaker 104 includes the docking projection 148 extending from a surface 302 at a docking end of a body 300. The docking projection 148 includes one or more docking surfaces, including edge docking surfaces 306, an end surface 308, and/or the like, configured to matingly engage corresponding cap surfaces disposed relative to the chamber 142 of the docking cap 136, thereby providing torque transmission to the leadless pacemaker 104. In one implementation, the edge docking surfaces 306 include one or more flat radial surfaces that may be radially symmetrical about the docking projection 148. The edge docking surfaces 306 may be disposed relative to the end surface 308 forming a ledge extending transverse to the end surface 308. In one implementation, the end surface 308 is flat and the surface 302 of the body 300 is flat providing additional surfaces for torque transmission.

Figure 11:
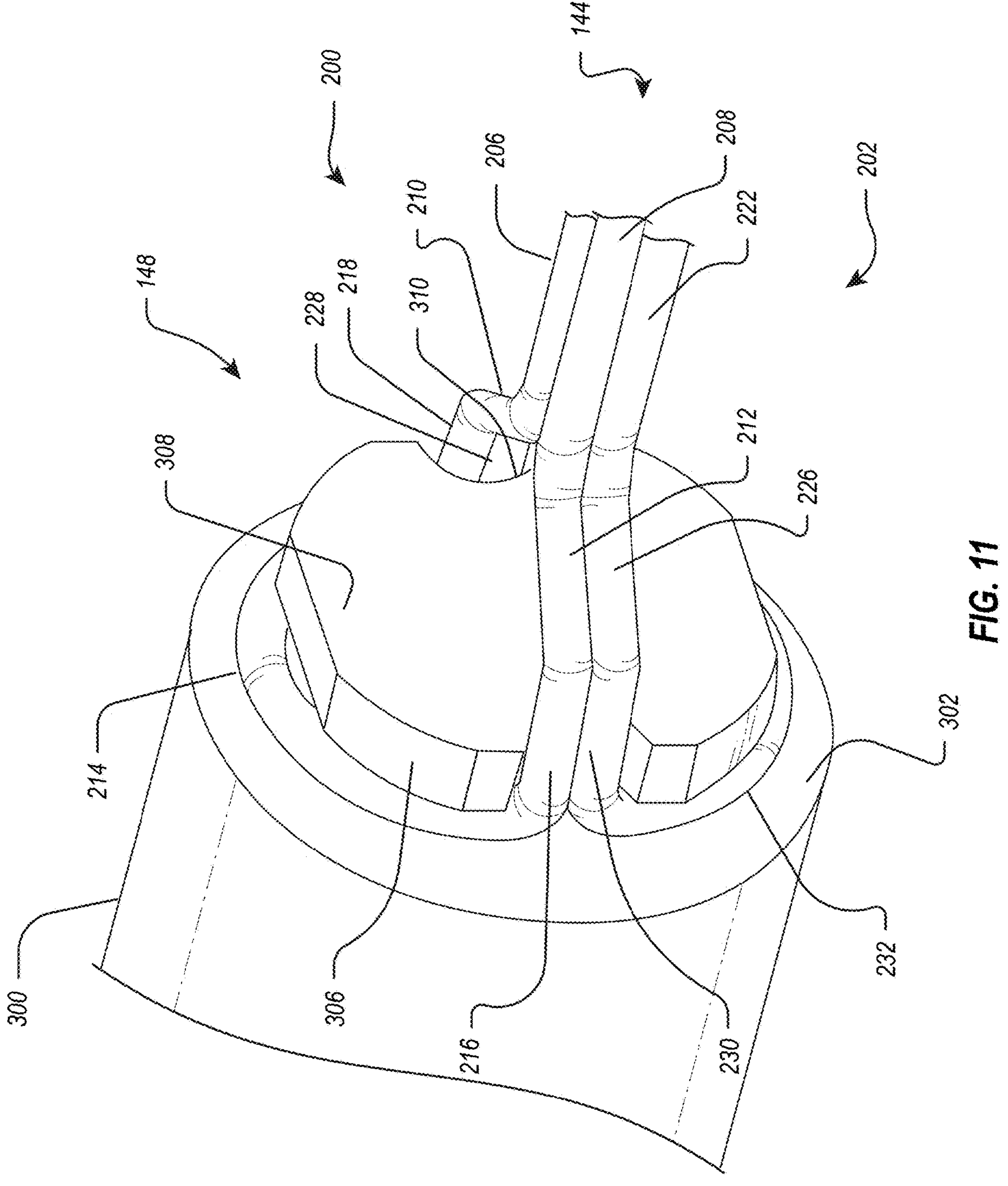
FIG. 11 illustrates an example flexible grasper engaged to a docking projection of a leadless pacemaker.

The docking surfaces may include one or more keys adapted to matingly engage corresponding features of the docking cap 136 and/or the retriever 144. The docking projection 148 and/or the surface 302 of the docking end of the body 300 may include one or more of the keys. In one implementation, the docking projection 148 includes side keys 310 extending through the docking projection 148 from the surface 302 of the body 300 to the end surface 308. The side keys 310 may be oriented relative to each other on opposite sides, such that they are radially symmetric. As shown in FIG. 11, in one implementation, the side keys 310 are adapted to matingly engage a portion of the first arm 200 and the second arm 202 of the retriever 144 in the engaged position. For example, the grasping portions 214, 216, 228, and 230 may be displaced during sheathing of the docking cap 136 into the side keys 310 where the docking cap 136 holds them in place in the engaged position. The side keys 310 may include one or more key surfaces 312 for torque transmission via the first arm 200 and the second arm 202 of the retriever 144.

Similarly, the docking projection 148 may include a neck 304 indented from the edge docking surfaces 306 and adapted to matingly engage at least a portion of the first arm 200 and the second arm 202 of the retriever 144. For example, the docking cap 136 may hinge the first and second looped portions 214 and 232 radially inwards into the neck 304, where the docking cap 136 holds the first and second looped portions 214 and 232 in compression around the docking projection 148 in the engaged position. The indentation of the neck 304 prevents the first and second arms 200 and 202 from translating longitudinally and disengaging from the docking projection 148. The geometry of the docking projection 148 facilitates a smooth capture and release by the retriever 144 when the docking cap 136 is sheathed distally or retracted proximally.

Figure 12:
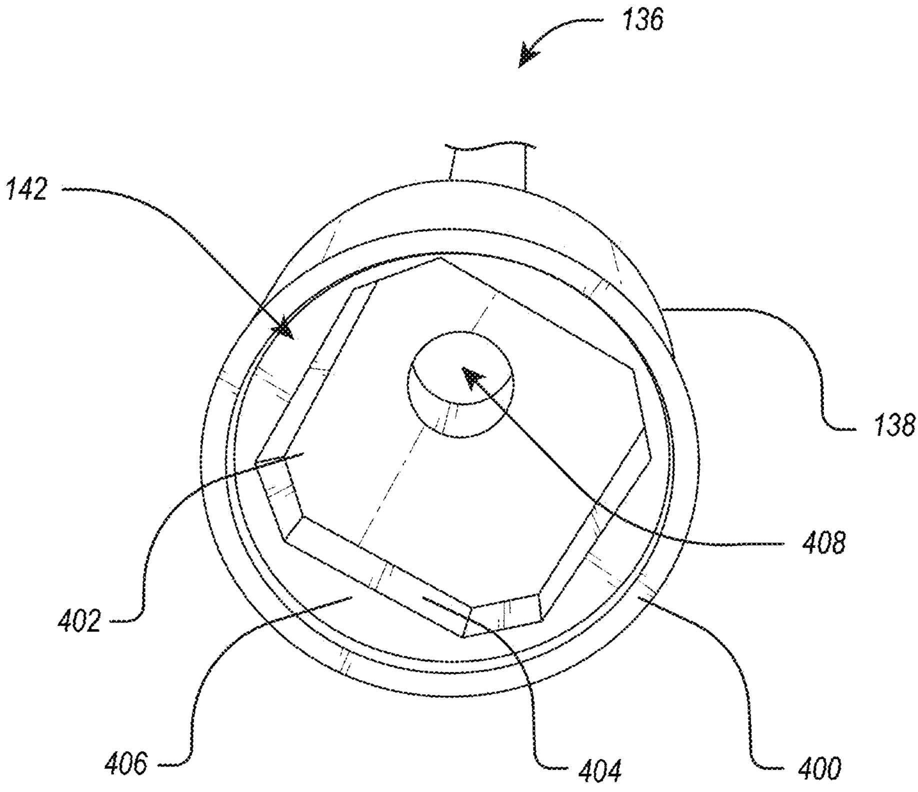
FIG. 12 shows a perspective front view of an example docking cap.

Referring to FIG. 12, the body 138 of docking cap 136 includes one or more cap surfaces disposed relative to the chamber 142 adapted to matingly engage the docking surfaces of the docking end of the leadless pacemaker 104 and/or features of the retriever 144. In one implementation, the one or more cap surfaces include a distal end surface 400, a proximal chamber surface 402, and one or more side surfaces 404 extending between the proximal chamber surface 402 and one or more ledge surfaces 406 disposed proximal to the distal end surface 400 within the chamber 142. The distal end surface 400 defines an opening into the chamber 132, and the proximal chamber surface 402 defines a proximal opening 408 into the chamber 142 extending through the receiving portion 140. The proximal opening 408 is coaxial with the longitudinal axis of a lumen of the torque shaft 114 and the retriever 144.

The ledge surfaces 406 may mirror a size and shape of the surface 302 of the docking end of the body 300 of the leadless pacemaker 104. For example, both the ledge surfaces 406 and the surface 302 may be flat. Similarly, the proximal chamber surface 402 may be sized and shaped to matingly engage the end surface 308 of the docking projection 148, and the side surfaces 404 matingly engage the edge docking surfaces 306. The mating engagement of each of the various cap surfaces with the corresponding docking surfaces provides torque transmission. When in the docking position, the engagement of the docking projection 148 with the docking cap 136 generates approximately 1.5 in-oz of torque with a mating normal force of approximately 500 g. The torque generated is thus an order of magnitude higher than the 0.125 in-oz or less of torque generally needed to implant a leadless pacemaker into human tissue.

Figure 13:
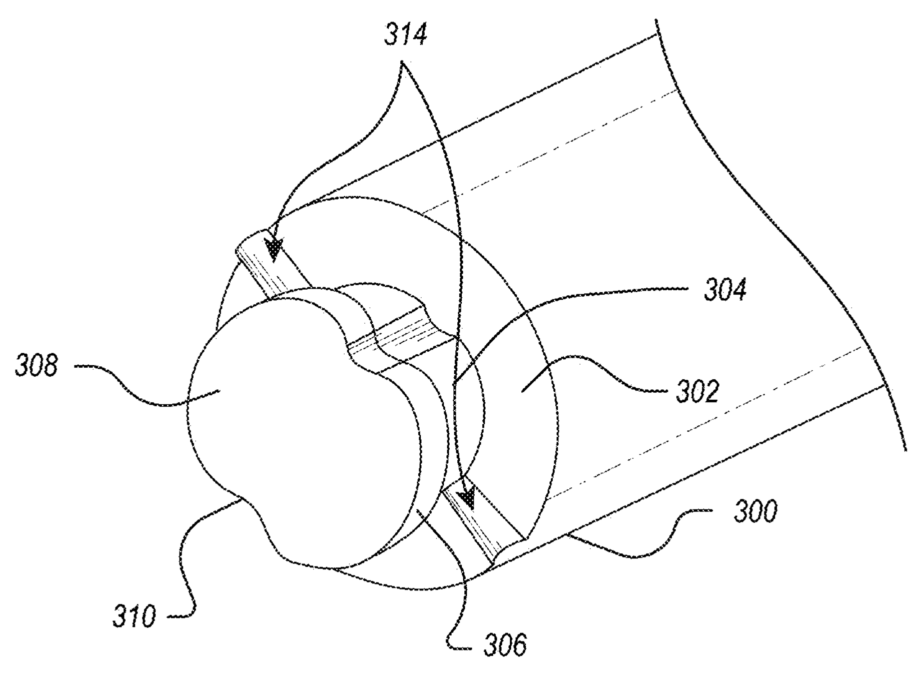
FIG. 13 shows a docking end of a leadless pacemaker with example keys defined in a surface.
Figures 14A, 14B, 14C:
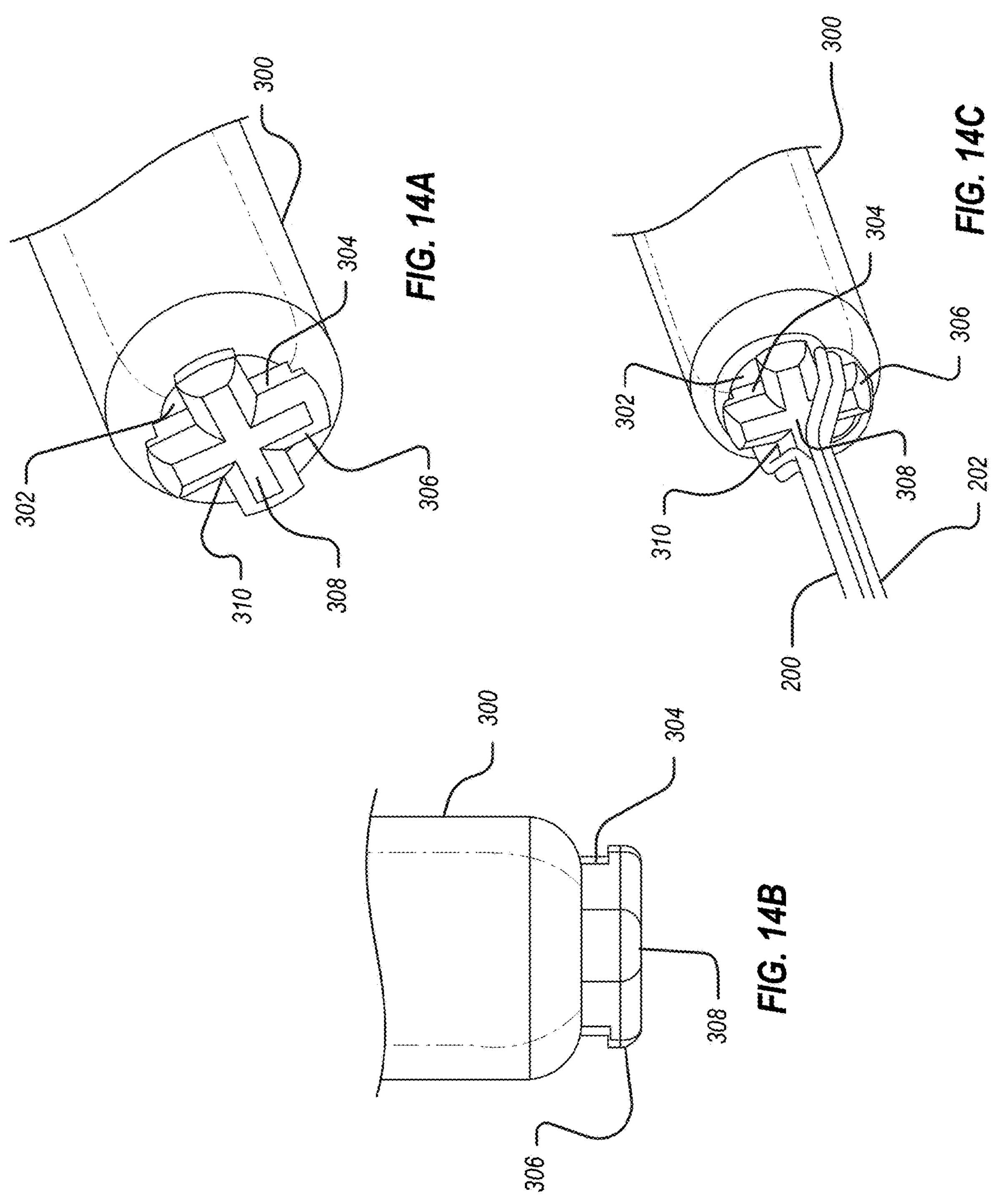
FIGS. 14A and 14B are perspective and top views, respectively, of an example docking projection having a cross shape.
FIG. 14C illustrates a flexible grasper engaged to the docking projection of FIGS. 14A-14B.
Figure 16B:
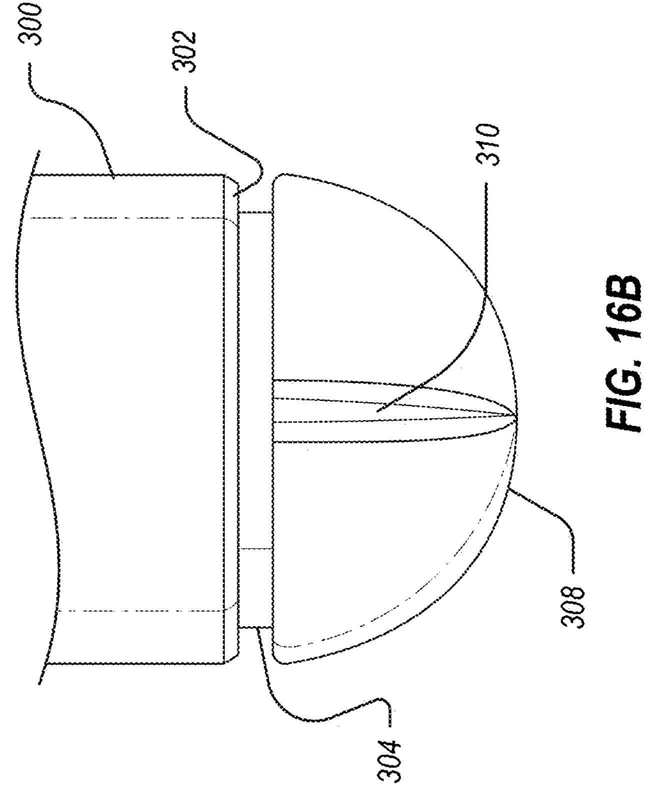
FIGS. 16A and 16B illustrate a perspective view and a top view, respectively, of an example set of keys defined in a surface of the docking projection.
Figure 16A:
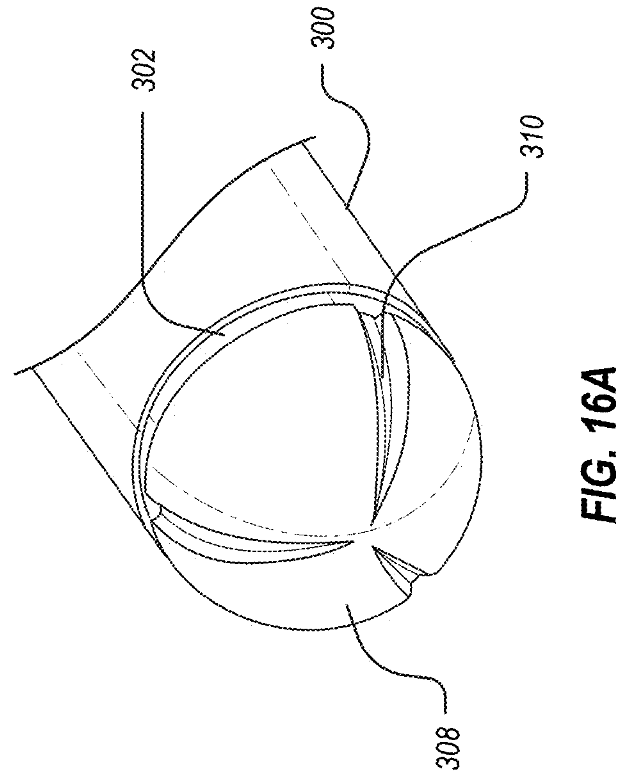

Examples of various geometries of the docking end of the leadless pacemaker 104 are shown in FIGS. 13-18. The geometries include one or more keys in the form of torque transmission keys, dimples, and/or geometric interference features that matingly engage with corresponding features on the docking cap 136. Turning first to FIG. 13, in one implementation, the surface 302 of the body 300 includes one or more undercut keys 314 defined therein. Alternatively or additionally, the docking projection 148 may have a cross-shape as shown in FIGS. 14A-14C with the side keys 310 forming angled cutouts.

In another implementation, the end surface 308 of the docking projection 148 is rounded, as shown in FIGS. 15A-18. A profile of the end surface 308 may have a variety of lengths from a lower profile curve to a higher dome shaped profile, each with the end surface 308 being a non-traumatic smooth round surface. The docking cap 136 includes corresponding cap surfaces mirroring the size and shape of the end surface 308 to hold the retriever 144 in compression against the docking projection 148 in the engaged position. Frictional contact between the cap surfaces and the end surface 308 provide torque transmission. To further facilitate torque transmission, the end surface 308 may include the keys 310 adapted to matingly engage cap keys 410, as can be understood from FIGS. 16A-18. To increase the friction of the mating surfaces, an overmolding 412 made from silicone or a similar material may be applied to the cap surfaces within the chamber 142 and/or on the docking projection 148, as shown in FIGS. 19A-19B.

Figure 17B:
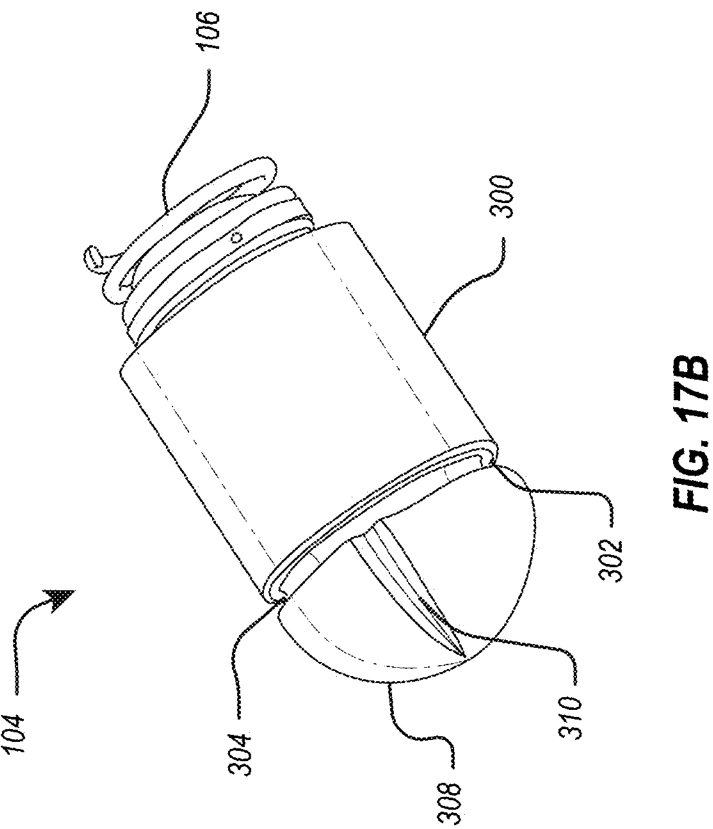
FIGS. 17A and 17B show a top view and a perspective view of an example leadless pacemaker having a round docking projection with a set of keys.
Figure 17A:
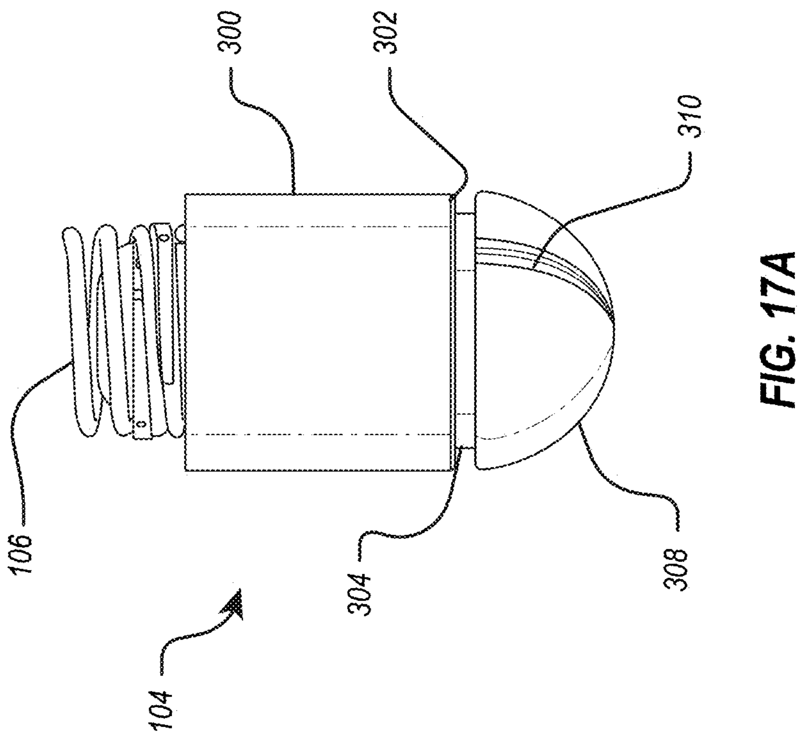
Figure 18:
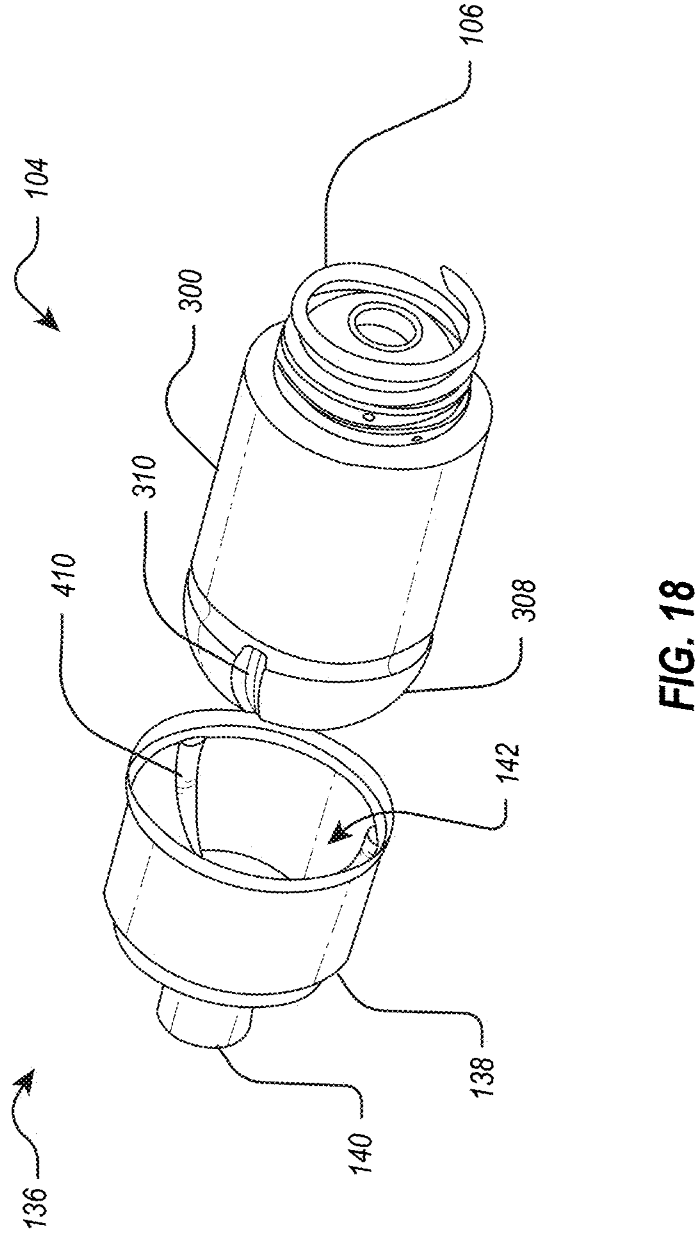
FIG. 18 depicts an example docking cap disposed relative to an example leadless pacemaker, the docking cap including one or more cap surfaces configured to mating engage one or more docking surfaces of the docking projection.
Figures 19A, 19B:
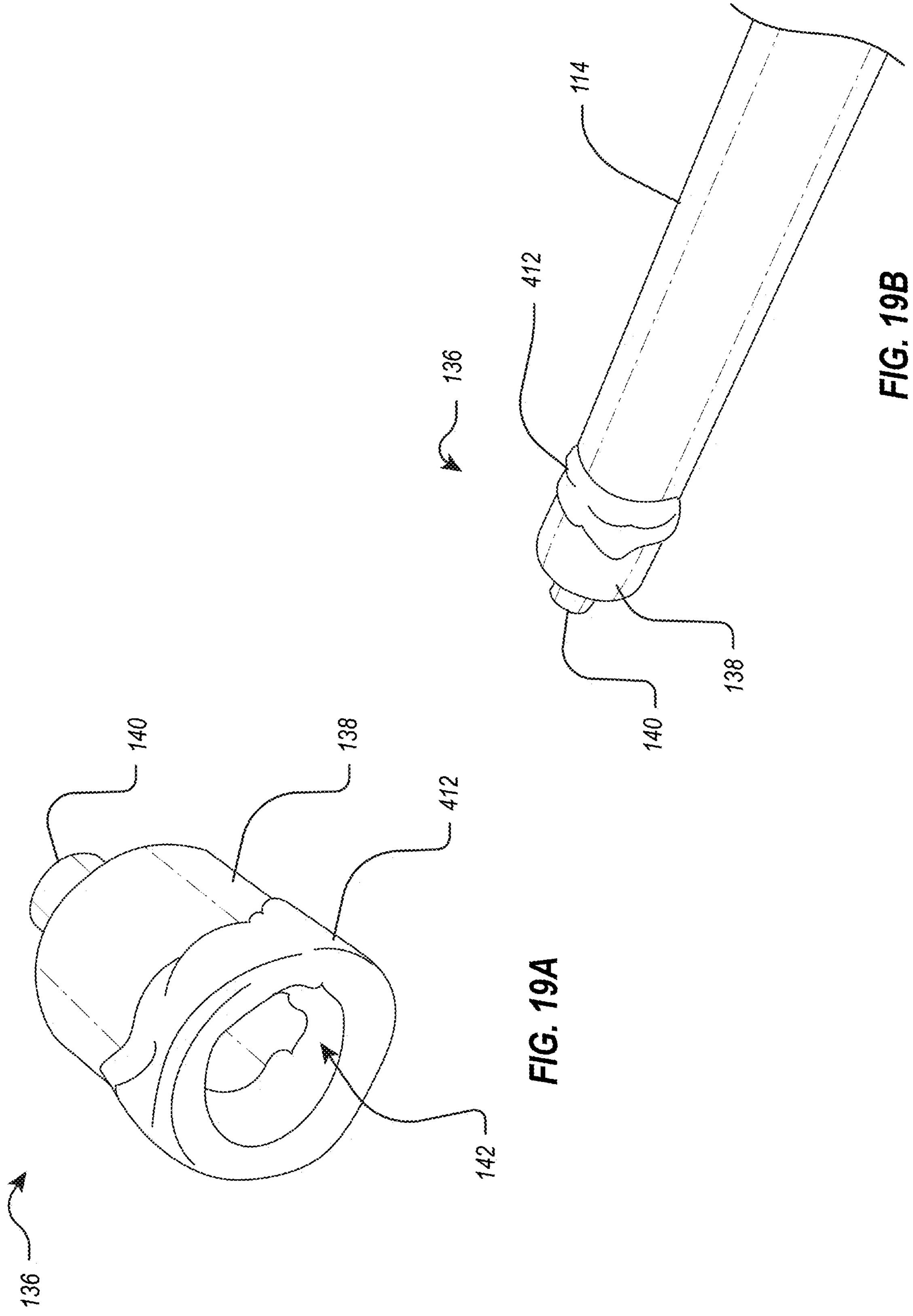
FIGS. 19A and 19B illustrating an example docking cap released from and engaged to a leadless pacemaker, respectively, the docking cap having an overmolding configured to transfer torque via increased friction between the docking cap and the leadless pacemaker.

Referring to FIGS. 17A-18, the helical anchor 106 is disposed on a fixing end of the leadless pacemaker 104 opposite the docking end. In one implementation, the fixing end is at the distal end of the leadless pacemaker 104, and the docking end is at the proximal end. It will be appreciated that some or all of these features may be reversed (standproud of their surface) depending on size restraints of the leadless pacemaker 104.

Figure 20:
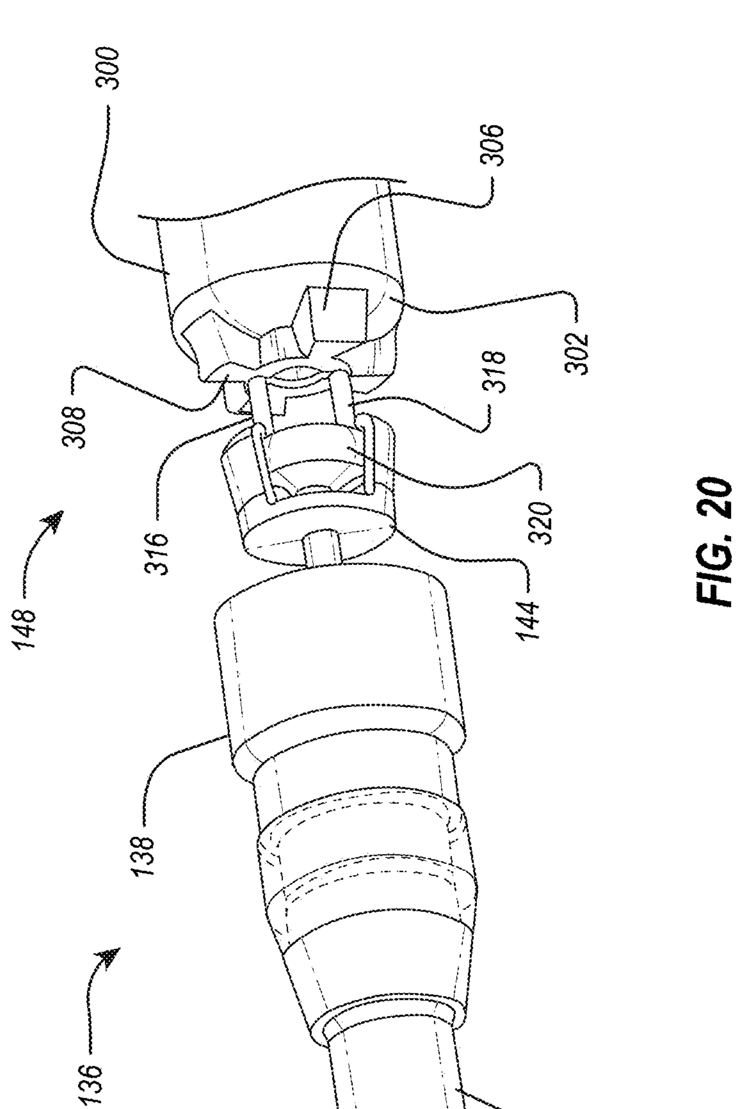
FIG. 20 illustrates another example retriever in the form of a flexible grasper engagable to a docking button.

For a detailed description of another example of the retriever 144 in the form of a flexible grasper and a corresponding example of the docking projection 148, reference is made to FIGS. 20-26C. Turning first to FIG. 20, in one implementation, the docking projection 148 includes a docking button 320 mounted to the end surface 308 with one or more posts (e.g., first and second posts 316 and 318). As can be understood from FIG. 21, the docking button 320 may be integral with the posts 316 and 318 and be a rounded surface extending between a first end 322 and a second end 324.

Figure 21:
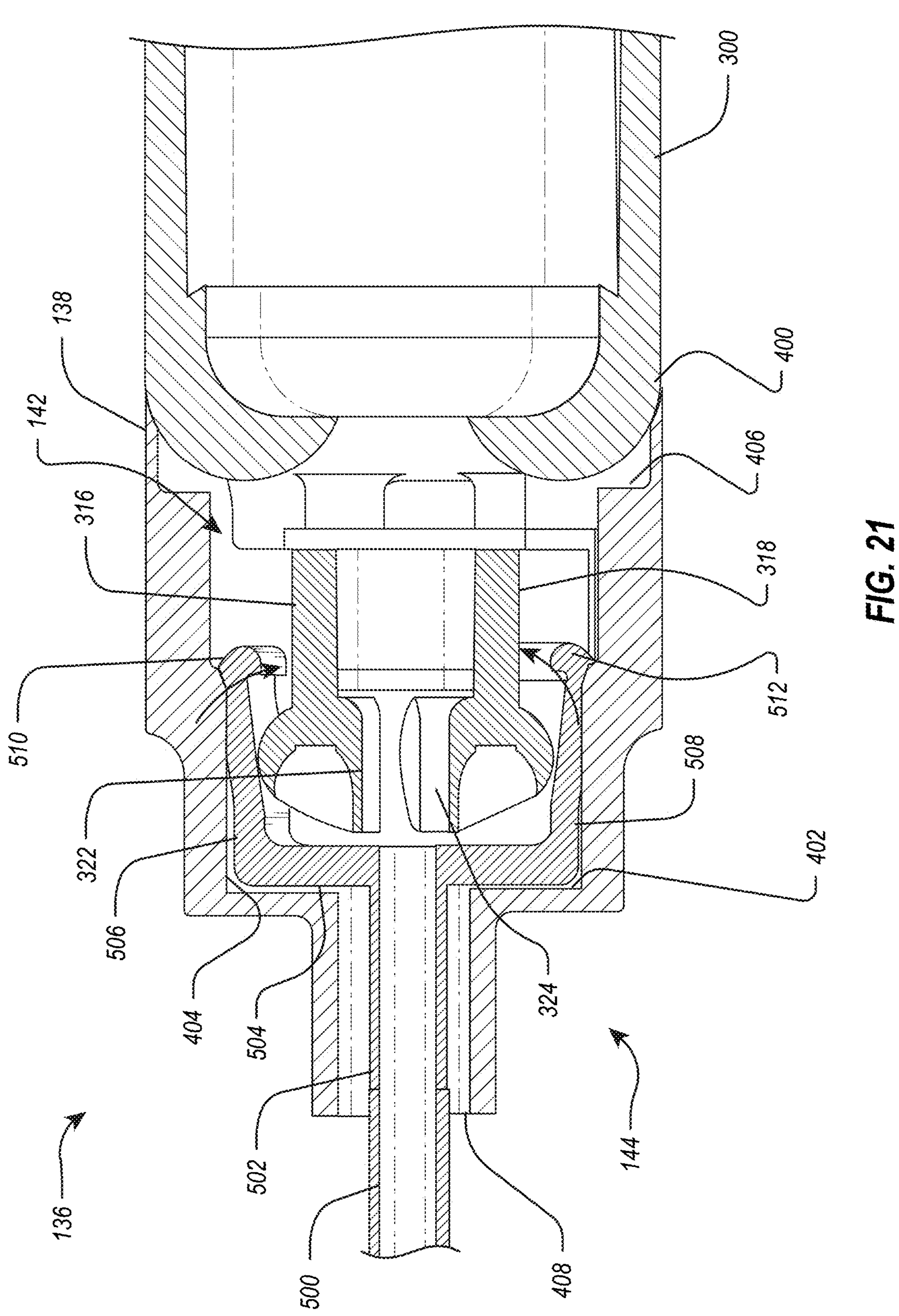
FIG. 21 is a cross-section of a docking cap holding arms of a flexible grasper in compression around a docking button within a chamber.
Figure 22:
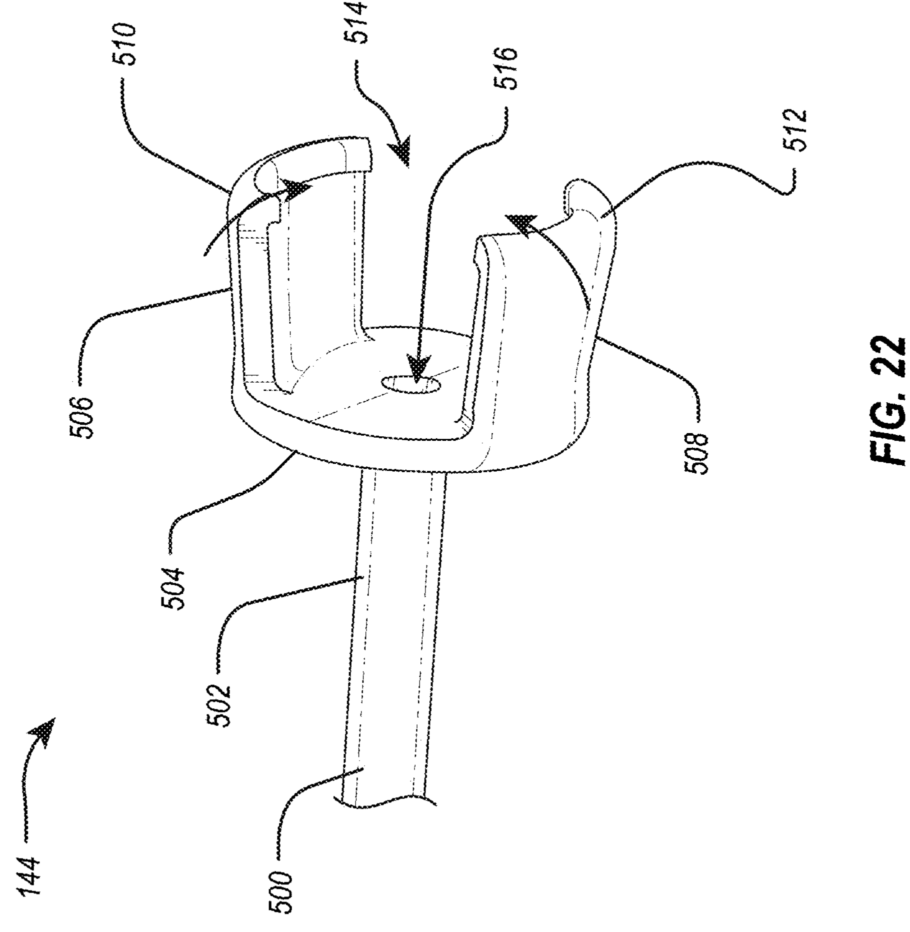
FIG. 22 is a detailed view of an example flexible grasper.

As shown in FIGS. 21 and 22, the retriever 144 includes a mandrel 500 connected to a base 504. The mandrel 500 may be connected directly to the base 504 or indirectly via a retriever shaft 502. The mandrel 500 extends through the proximal opening 408 and into the lumen of the torque shaft 114. The retriever 144 may be made from a variety of elastic or otherwise flexible materials, including, but not limited to, a polymer (e.g., polyether ether ketone (PEEK)), Nitinol or other memory wire, cable, tubing, and/or the like.

The retriever 144 includes a first arm 506 and a second arm 508 extending from the base 504 and defining a docking space 514 therebetween. In one implementation, the first and second arms 506 and 508 form a jaw with hinges adapted to grasp at least a portion of the docking projection 148, such as the docking button 320, in the docking space 514 when the docking cap 136 is sheathed over retriever 144 into the docked position. In another implementation, one or more hinges are disposed at the connection points between the arms 506 and 508 and the base 504. The first arm 506 may include a first lip 510, and the second arm 508 may include a second lip 512. Each of the lips 510 and 512 extends inwardly towards a longitudinal axis of a lumen 516 of the retriever 144.

Figure 23:
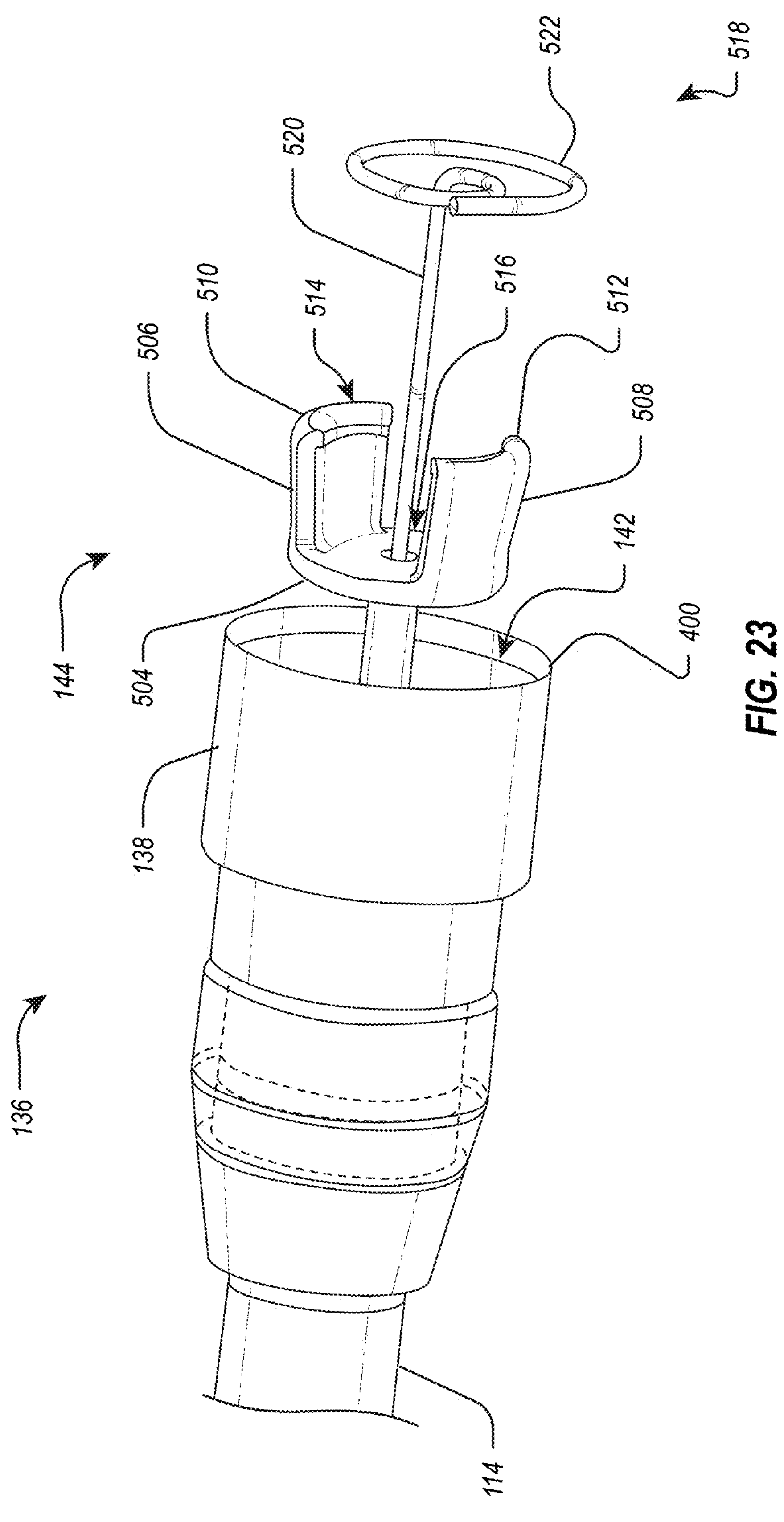
FIG. 23 shows a tether extending through a lumen of an example flexible grasper.

As illustrated in FIG. 23, in one implementation, a tether 518 may be introduced during a tether mode or test mode to check for thresholds, among other reasons. The tether 518 may be, without limitation, a snare, a flexible shaft, and/or the like. For example, the tether 518 may include an elongated body 520 extending distally through the lumen 516 of the retriever 144 to a distal loop 522.

Figure 24:
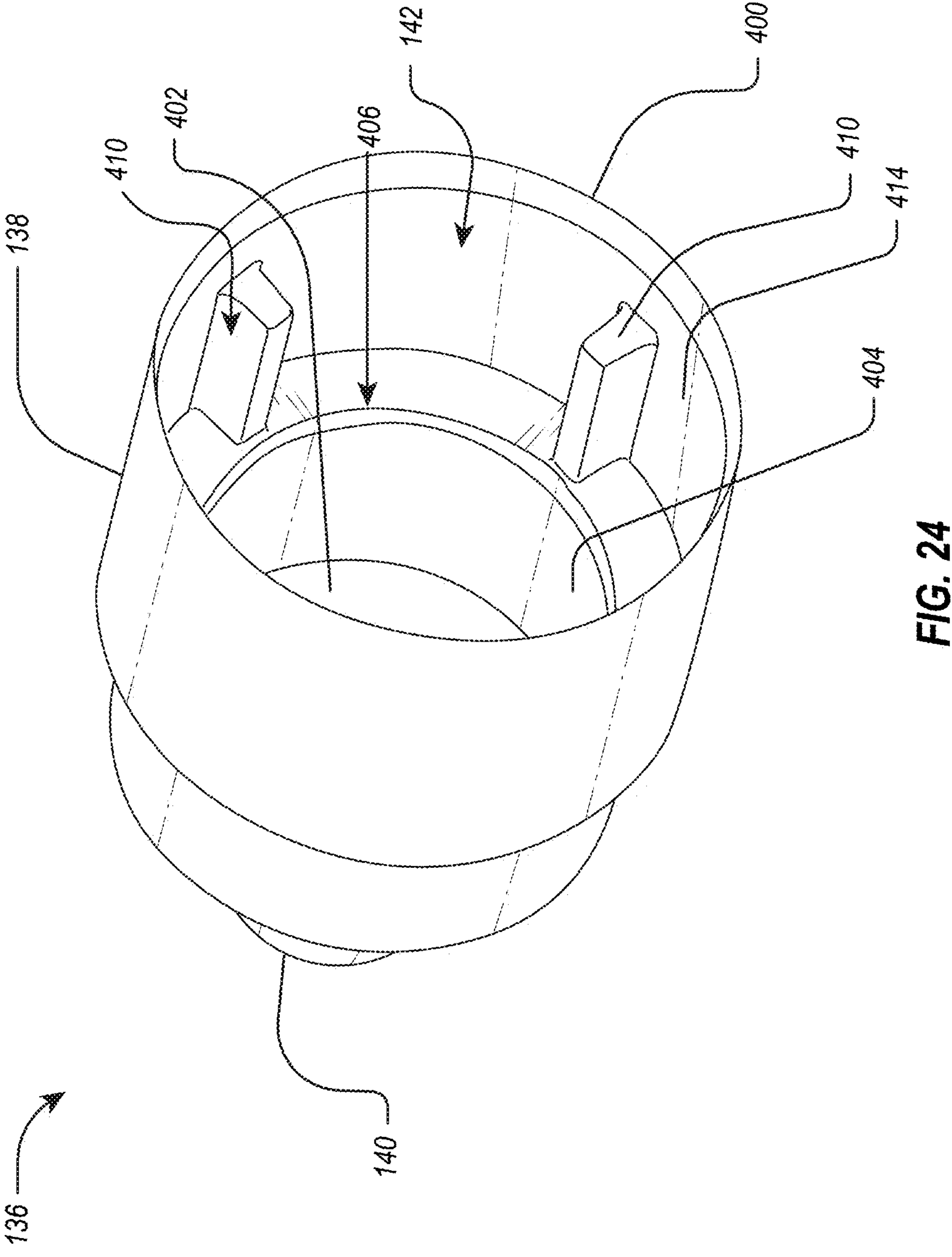
FIG. 24 depicts an example docking cap.

Turning to FIG. 24, another example of the docking cap 136 is shown. The body 138 of the docking cap 136 includes one or more cap surfaces, as described herein, adapted to provide torque to the leadless pacemaker 104 via the docking surfaces of the docking end of the leadless pacemaker 104, as well as to move the first arm 506 and the second arm 508 to the engaged position around the docking projection 148. In one implementation, the one or more cap surfaces are disposed relative to the chamber 142 and are adapted to matingly engage the docking surfaces and/or features of the retriever 144. The one or more cap surfaces may include the distal end surface 400, the proximal chamber surface 402, and the side surface 404 extending between the proximal chamber surface 402 and the ledge surface 406, which is disposed proximal to the distal end surface 400 within the chamber 142. The distal end surface 400 defines an opening into the chamber 132, and the proximal chamber surface 402 defines the proximal opening 408 into the chamber 142 extending through the receiving portion 140. The proximal opening 408 is coaxial with the longitudinal axis of a lumen of the torque shaft 114 and/or the steerable catheter 118 and the lumen 516 of the retriever 144.

The ledge surface 406 may mirror a size and shape of the surface 302 of the docking end of the body 300 of the leadless pacemaker 104. For example, both the ledge surface 406 and the surface 302 may be flat. The mating engagement of each of the various cap surfaces with the corresponding docking surfaces provides torque transmission. To further facilitate torque transmission, one or more of the cap surfaces may include the cap keys 410. In one implementation, the cap keys 410 are disposed radially around a distal side surface 414 extending from the ledge surface 406 towards the distal end surface 400. The cap keys 410 may be adapted to matingly engage corresponding side keys 310 defined in the docking projection 148 for torque transmission.

Figures 25A, 25B:
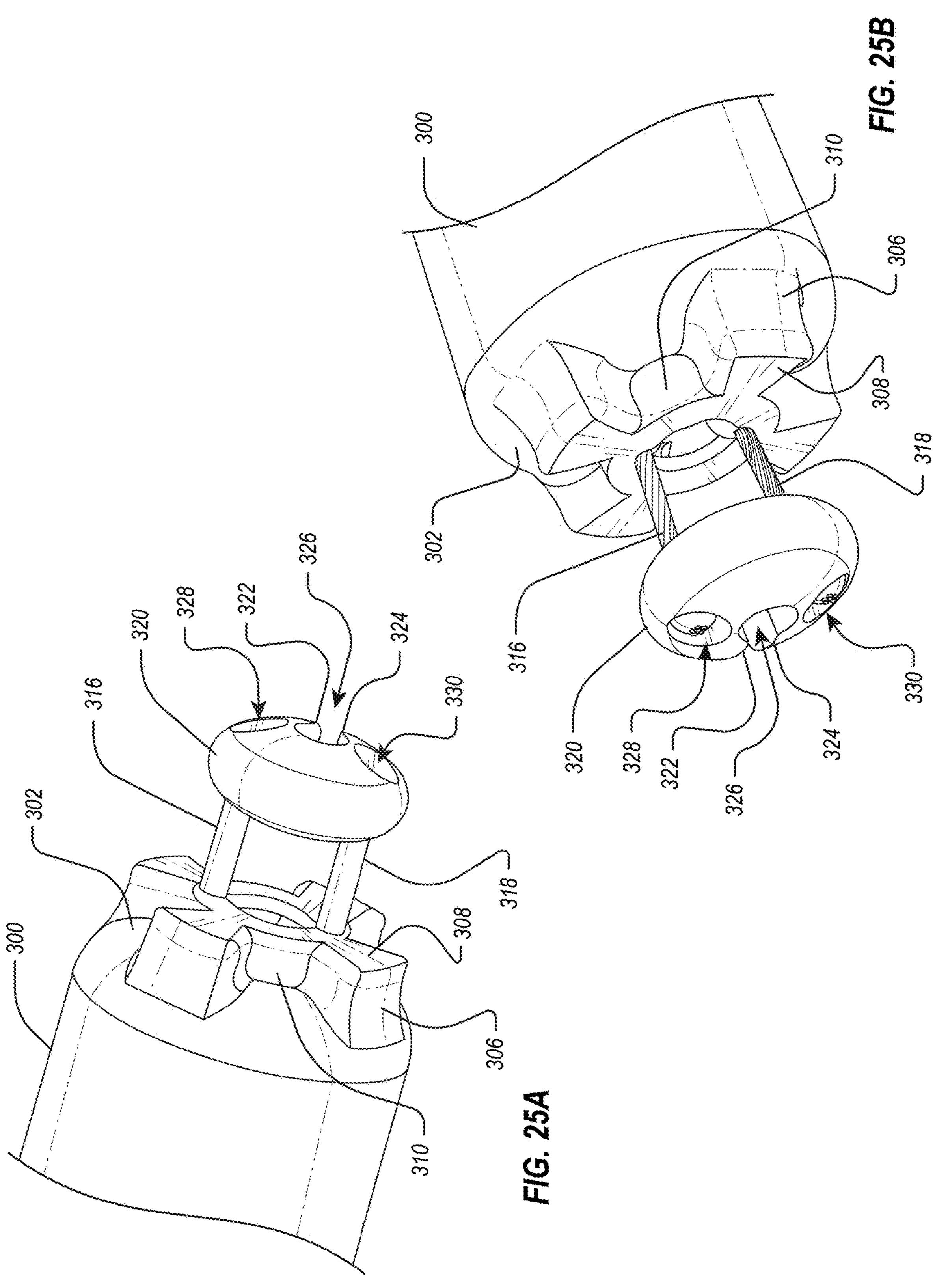
FIGS. 25A and 25B illustrate a rigid docking button and a flexible docking button, respectively.

Additional examples of the docking projection 148 are shown in FIGS. 25A-25B. In one implementation, the side keys 310 are defined in the edge docking surfaces 306 of the docking projection 148 extending from the surface 302 of the body 300 to the end surface 308. The side keys 310 may be oriented relative to each other on opposite sides, such that they are radially symmetric. In one implementation, the cap 136 is adapted to matingly engage the docking projection 148 with the edge docking surfaces 306 disposed along the distal side surface 414 and the cap keys 410 disposed within the side keys 310.

The ledge surface 406 may be adapted to displace the first arm 506 and the second arm 508 radially inward from their natural state in which they are biased radially outwards. In one implementation, the ledge surface 406 displaces the first and second arms 506 and 508 until they close around the docking button 320 in the engaged position shown in FIG. 21. The side surface 404 holds the first and second arms 506 and 508 around the docking button 320 with the first and second lips 510 and 512 extending inwardly past an outer edge of the docking button 320, preventing the docking button 320 from translating distally out of the docking space 514 and thus releasing from the retriever 144.

The docking button 320 may be mounted to the end surface 308 with the first and second posts 316 and 318. As can be understood from FIG. 25A-25B, the docking button 320 may be integral with, connected rigidly to, and/or connected flexibly to the posts 316 and 318. In one implementation, the docking button 320 is a rounded surface extending between the first end 322 and the second end 324, which are separated by a gap opening into a button lumen 326. The docking button 320 includes a first slot 328 and a second slot 330 adapted to receive and engage the first and second posts 316 and 318, respectively.

Figure 26A:
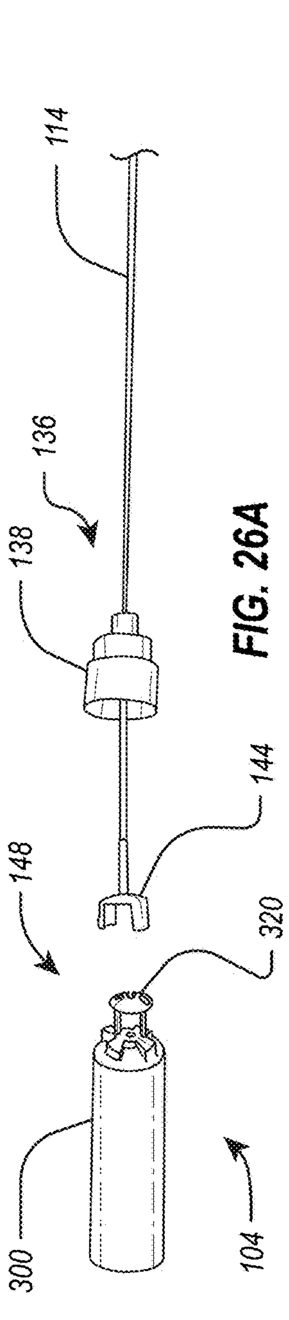
FIG. 26A shows a flexible grasper disposed relative to a docking button of a leadless pacemaker.
Figure 26B:
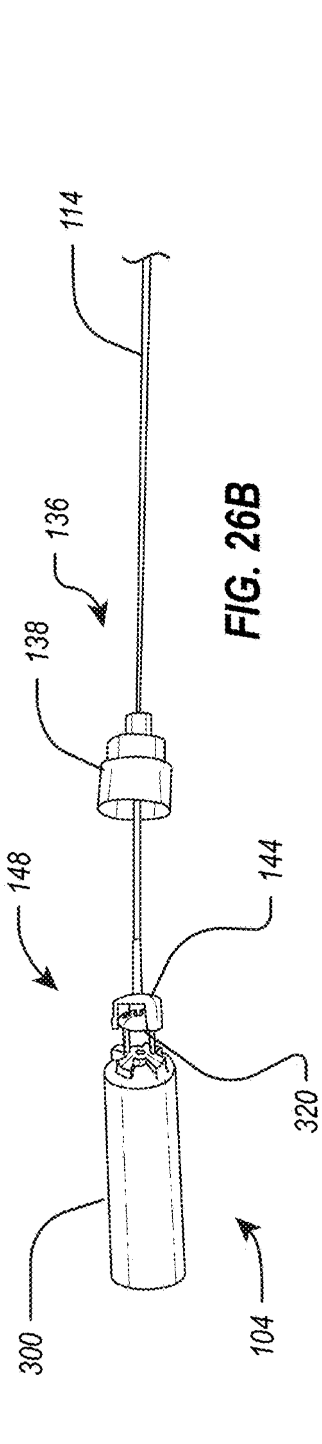
FIG. 26B illustrates the docking button positioned between a first arm and a second arm of the flexible grasper.
Figure 26C:
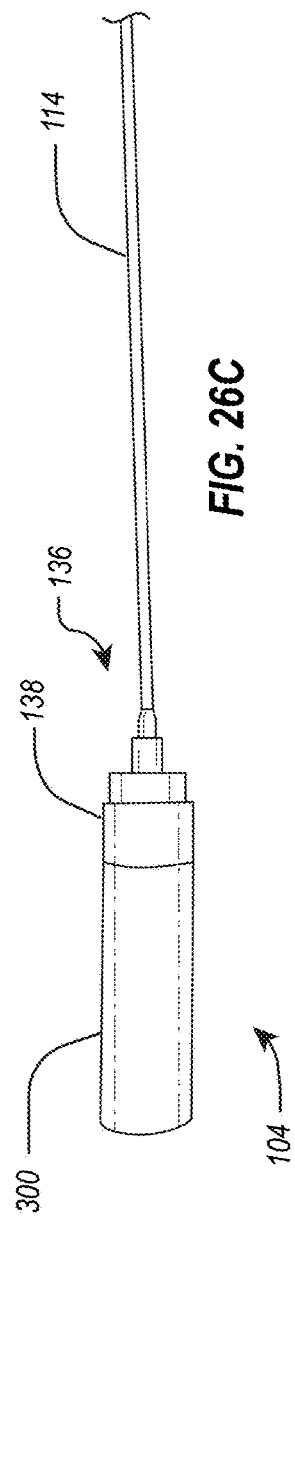
FIG. 26C shows a docking cap sheathed over the flexible grasper and holding the first arm and the second arm in compression around the docking button.

For a detailed description of docking and releasing the leadless pacemaker 104 for delivery and/or retrieval, reference is made to FIGS. 26A-26C. In one implementation, the retriever 144 is disposed relative to the docking projection 148. FIG. 26A illustrates the retriever 144 approaching the docking projection 148 for engagement. The docking projection 148 is positioned in the docking space 514 between the first and second arms 506 and 508. For example, the docking button 320 of the docking projection 148 may be positioned within the docking space 514, as shown in FIG. 26B. The body 138 of the docking cap 136 is sheathed over the retriever 144 until the docking end of the leadless pacemaker 104 including the docking projection 148 is disposed within the chamber 142. The docking cap 136 holds the retriever 144 in compression around the docking button 320 locking the leadless pacemaker 104 in the docked position shown in FIG. 26C. The leadless pacemaker 104 is thus docked to the catheter system 108 and prepared for delivery through the patient anatomy to the implant site, for example, within the patient heart 102. The engagement of the docking cap 136 with the docking end of the leadless pacemaker 104 may be strong enough to maintain the leadless pacemaker 104 in the docked position against the force of gravity.

Once disposed within the implant site, the catheter system 108 is rotated using the handle body 122. The mating engagement of the one or more cap surfaces with the one or more docking surfaces transmits the torque of this rotation to the leadless pacemaker 104 to fix the leadless pacemaker 104 to the tissue at the implant site using the helical anchor 106. In some implementations, the tether 518 is used to check for thresholds. Once the leadless pacemaker 104 is fixed in the implant site, the catheter system 108 releases the leadless pacemaker 104. In one implementation, the body 138 of the docking cap 136 is retracted proximally until the retriever 144 is outside the chamber 142, causing the first arm 506 and the second arm 508 to spring open in a direction radially outwardly, thereby releasing the docking button 320. The catheter system 108 is then retracted along the patient anatomy and removed from the body.

During retrieval, the catheter system 108 is introduced into the body and advanced through the patient anatomy to the implant site until the retriever 144 is disposed relative to the docking projection 148. The retriever 144 is advanced until the docking button 320 is positioned within the docking space 514 between the first and second arms 506 and 508. The body 138 of the docking cap 136 is sheathed over the retriever 144, locking the leadless pacemaker 104 to the catheter system 108 in the docked position, as described herein. The catheter system 108 is then rotated with the mating engagement of the docking projection 148 with the docking cap 136 transmitting the torque to the leadless pacemaker 104 to unfix the helical anchor 106 from the tissue. The retriever 144 or other features of the catheter system 108, such as a cutting edge, may be used to remove any tissue overgrowth on the leadless pacemaker 104. The leadless pacemaker 104 is maintained in the docked position and the catheter system 108 is retracted through the patient anatomy to retrieve the leadless pacemaker 104.

Figure 27:
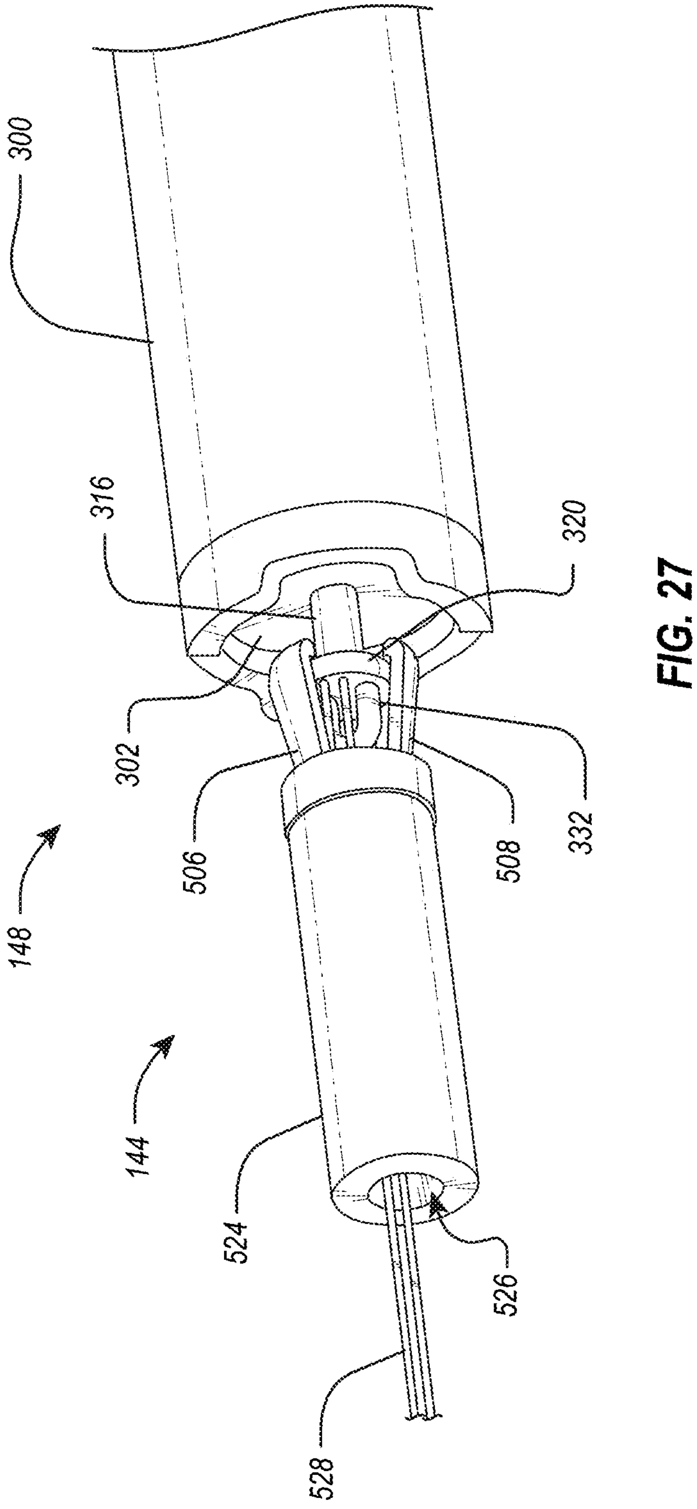
FIG. 27 illustrates an example docking projection having a loop configured to receive a tether, a snare, or a cable.

For another example of a docking cap adapted to lock the retriever 144 in the engaged position around the docking projection 148, reference is made to FIG. 27. In one implementation, the docking cap includes an elongated body 524 with a lumen 526 defined therein. A tether 528, which may be a snare, cable, or other tether, extends through the lumen 526 of the elongated body 526, as well as the lumen 516 of the retriever 144. The tether 528 may be looped through the docking projection 148 and taken back to the handle body 122 of the catheter system 108.

In one implementation, the docking projection 148 of the leadless pacemaker 104 includes the docking button 320 attached to the surface 302 of the body 300 of the leadless pacemaker 104 with the post 316. The docking button 320 includes a flat distal surface from which a hook 332 extends. The tether 528 may be looped through the hook 332.

To engage the retriever 144 in the docked position with the docking projection 148, the elongated body 524 is translated distally over the first arm 506 and the second arm 508 locking the docking button 320 in the engaged position within the docking space 514, as described herein. To release the leadless pacemaker 104, the elongated body 526 is translated proximally until the first and second arm 506 and 508 spring radially outwards to the natural state, thereby disengaging the docking button 320.

Figure 28:
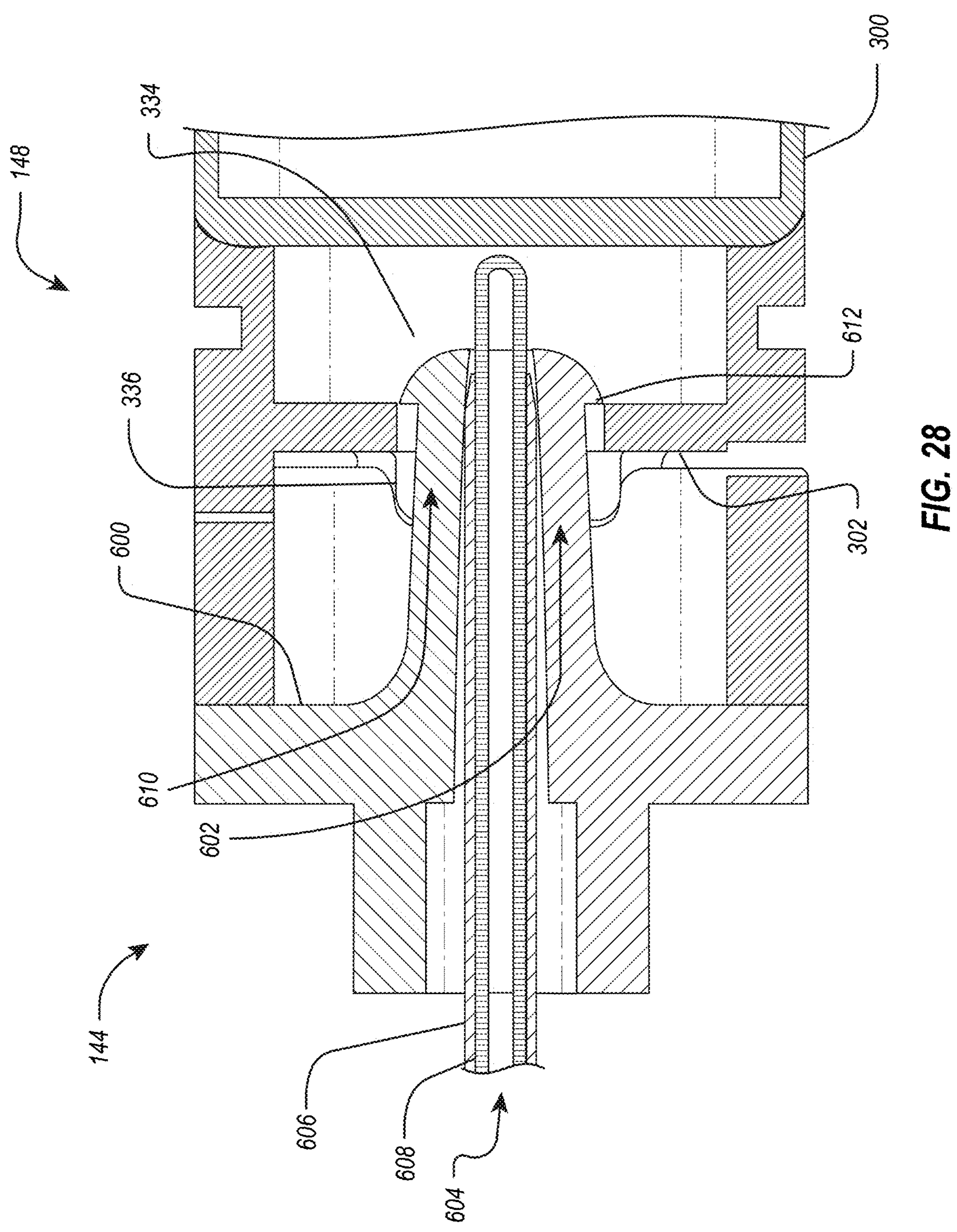
FIG. 28 is a cross-section of a retriever engaging a surface of a docking end of a leadless pacemaker within an opening in the surface.
Figure 29:
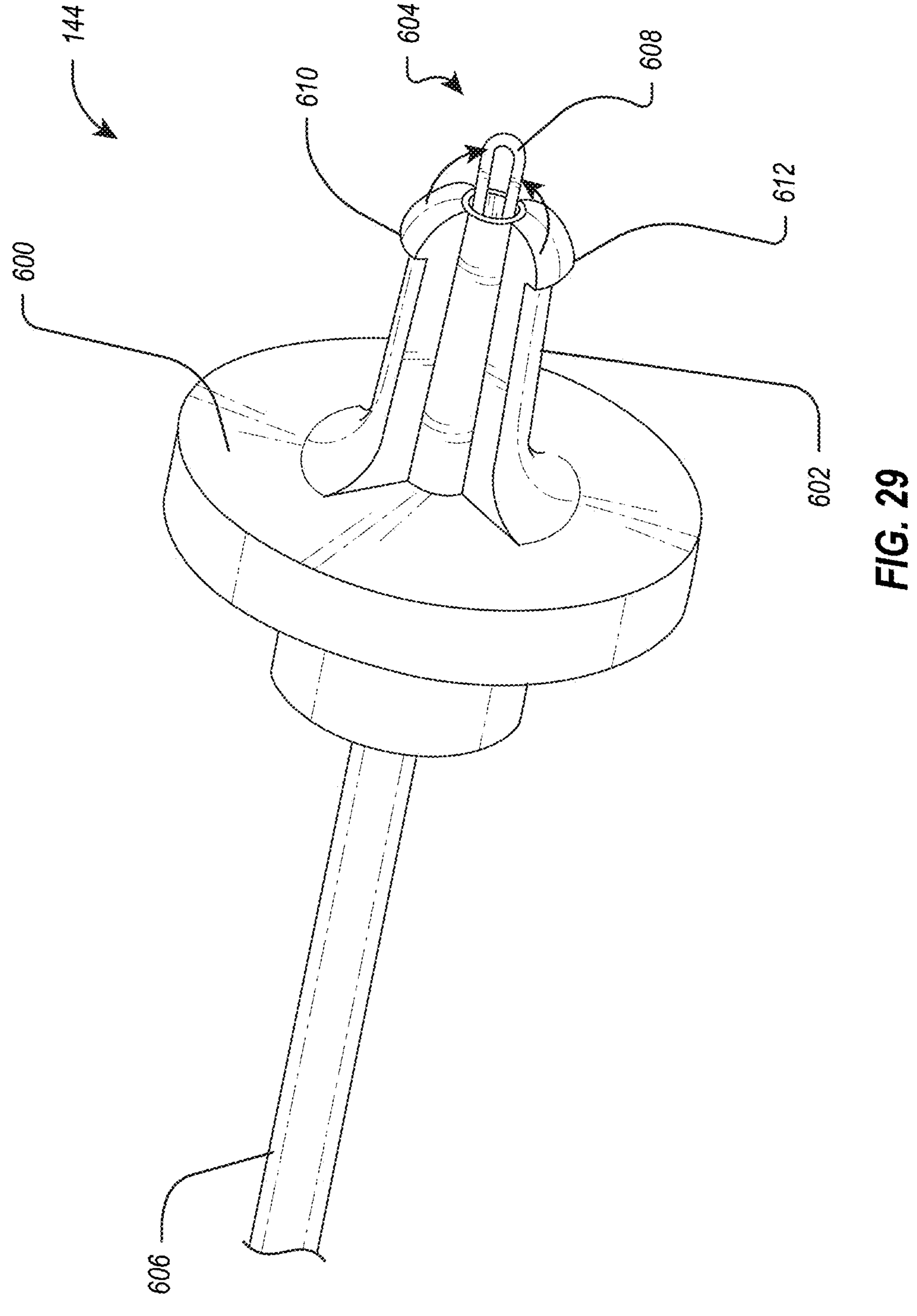
FIG. 29 shows a retriever having inwardly biased arms.

Turning to FIGS. 28 and 29, another example of the retriever 144 is shown. In one implementation, the retriever 144 includes a retriever base 600 from which a set of arms 602, including a first arm disposed opposite a second arm around a central lumen 604, extends. In one implementation, the set of arms 602 are disposed on and/or integral with a retriever shaft 606 extending through the retriever base 600. The central lumen 604 extends through the retriever shaft 606, the retriever base 600, and through the set of arms 602.

The set of arms 602 are biased radially inwards towards the central lumen 604 in a natural state. In one implementation, a mandrel 608 is translated within the central lumen 604 to move the set of arms 602 between an engaged and disengaged position with the docking projection 148. More particularly, the docking projection 148 may include a docking surface opening 334 defined within a docking surface 336 extending from or otherwise part of the surface 302 of docking end of the body 300 of the leadless pacemaker 104. The set of arms 602 include a first tab 610 and a second tab 612 each extending radially outwards from the central lumen 604. In the disengaged or natural state, the set of arms 602 are biased radially inwards, such that the set of arms 602 may be advanced through the docking surface opening 334. The mandrel 608 is advanced distally through the central lumen 604 pushing the set of arms 602 apart elastically, such that the first tab 610 and the second tab 612 are displaced radially outwards, thereby engaging the edges defining the docking surface opening 334 and locking the retriever 144 to the docking projection 148.

To disengage the retriever 144 from the docking projection 148 to release the leadless pacemaker 104, the mandrel 608 is retracted proximally within the central lumen 604, causing the set of arms 602 to spring radially inwards to the natural state. The first and second tabs 610 and 612 thus disengage the edges defining the docking surface opening 334, permitting the catheter system 108 to be retracted.

Figure 30A:
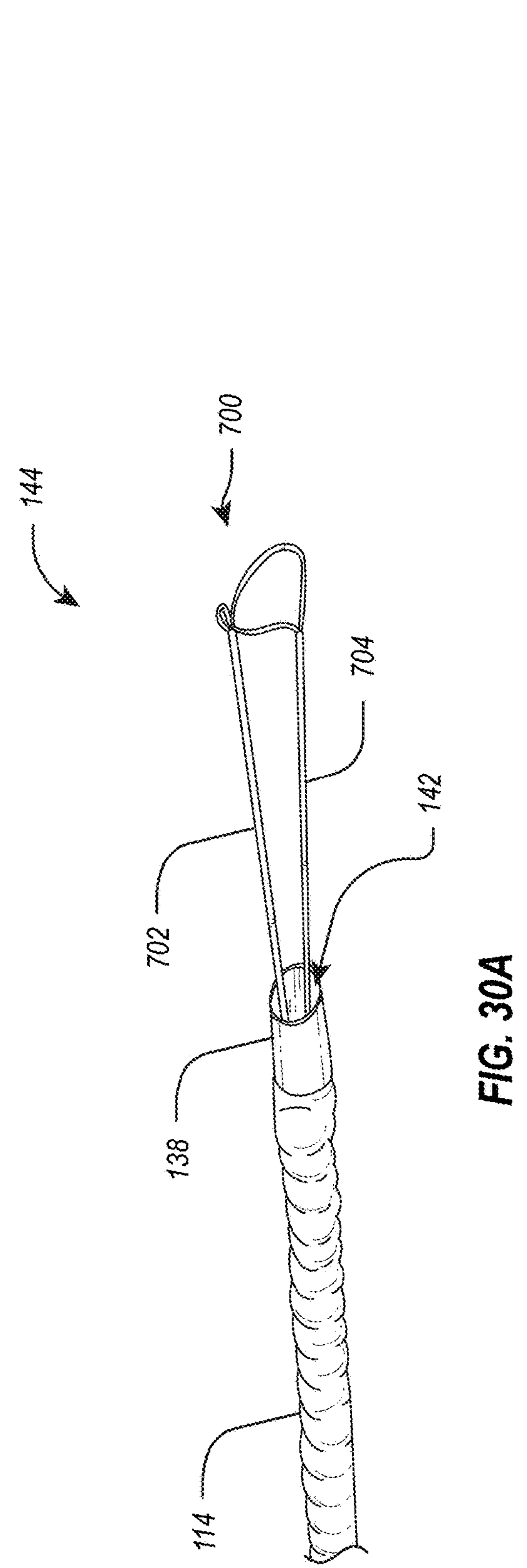
FIGS. 30A and 30B show an example retriever in the form of a snare extending from a set of sheaths.
Figure 30B:
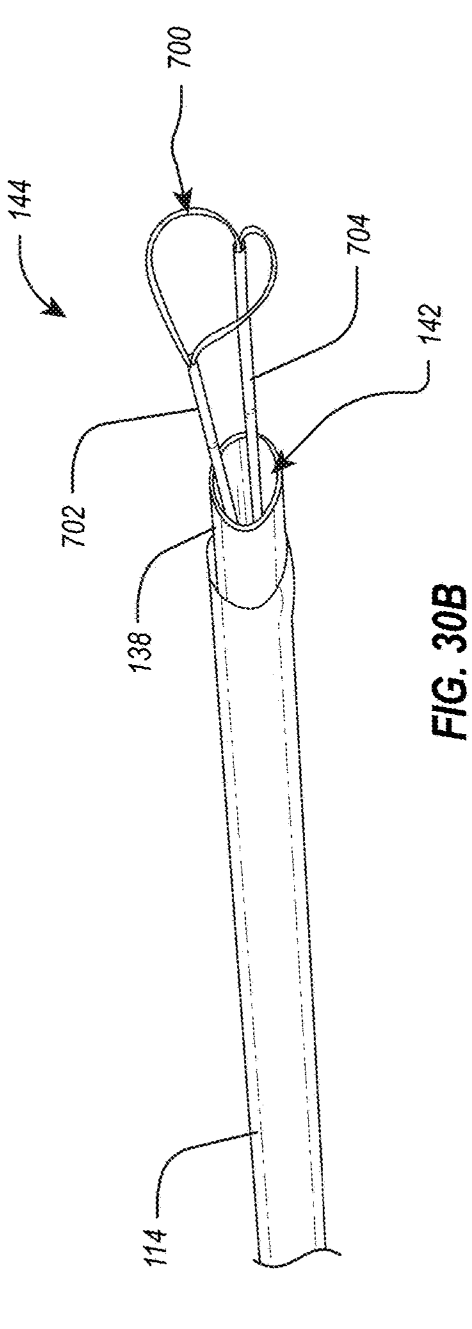

For a detailed description of examples of the retriever 144 in the form of a snare loop, reference is made to FIGS. 30A-40. Turning first to FIGS. 30A-30B, in one implementation, the body 138 of the docking cap 136 is fixed to a component of the catheter system 108, such as the torque shaft 114. The chamber 142 of the docking cap 136 is coaxial with a lumen of the catheter system 108, including, for example, a lumen of the torque shaft 114.

In one implementation, the retriever 144 includes a first sheath 702 and a second sheath 704 extending distally from the chamber 142. The first and second sheaths 702 and 704 may extend through the chamber 142 proximally into the lumen of the catheter system 108. The first and second sheaths 702 and 704 each translate longitudinally through the chamber 142 and the lumen of the torque shaft 114.

A snare 700 extends distally from and is translatable within the first and second sheaths 702 and 704. The snare 700 is configured to move between an engaged and disengaged position to releasably engage the docking projection 148. The first and second sheaths 702 and 704 may be made from a variety of materials, including, but not limited to, steel, elastic cable tubes, braided or coiled Polytetrafluoroethylene (PTFE) impregnated polyimide tubes, and/or the like. The snare 700 may be made from a variety of flexible materials, such as Nitinol or other elastic materials.

Figures 31A, 31B:
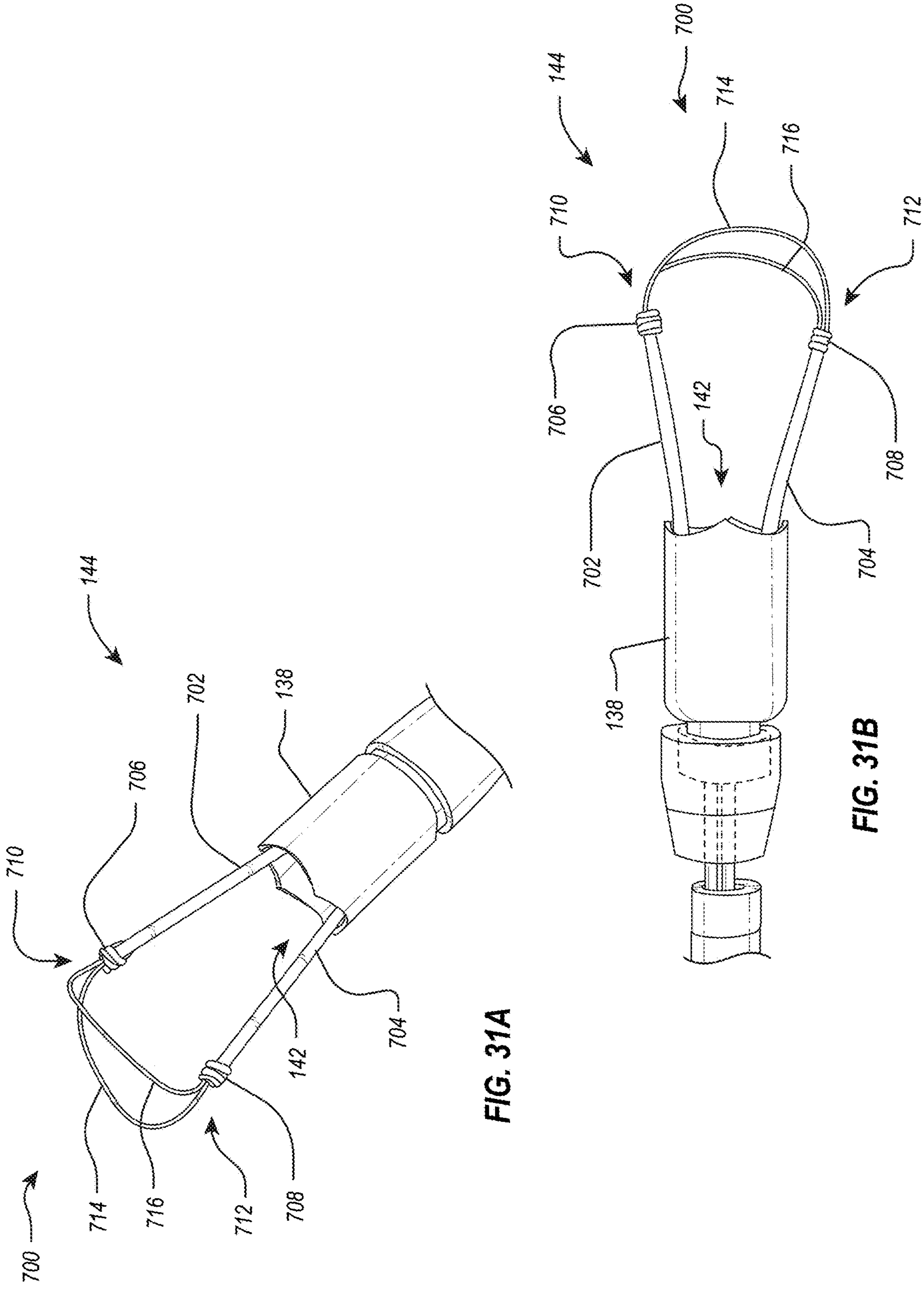
FIGS. 31A and 31B show detailed views of example snares.

Turning to FIGS. 31A and 31B, in one implementation, the snare 700 extends from and is translatable within a first snare lumen 710 of the first sheath 702 and a second snare lumen 712 of the second sheath 704. The snare 700 moves between the engaged and disengaged positions within the first and second snare lumens 710 and 712 to capture and release the docking projection 148 of the leadless pacemaker 104. In one implementation, the first sheath 702 includes a first end coil 706, and the second sheath 704 includes a second end coil 708. Radiopacity may be obtained by making the first and second end coils 706 and 708 radiopaque. Alternatively or additionally, a NiTi DFT composite wire combining Nitinol with Titanium or Platinum in varying sheath-to-core ratios, a Tungsten or Tantalum strand in NiTi cable, and/or the like may be used for radiopacity. Further, radiopaque coils and/or marker bands may be crimped or otherwise attached to the snare 700, radiopaque coils may be wound around an NiTi core, and/or the like.

In one implementation, the snare 700 includes a first snare wire 714 and a second snare wire 716. The first snare wire 714 extends from the first snare lumen 710 into the second snare lumen 712 forming a first snare loop pointing in a first direction, and the second snare wire 716 extends from the first snare lumen 710 into the second snare lumen 712 forming a second snare loop pointing in a second direction. In one implementation, the first direction is different from the second direction, forming a docking space therebetween. The first direction may be oriented relative to the second direction such that the snare 700 forms a duckbill shape.

Figure 32:
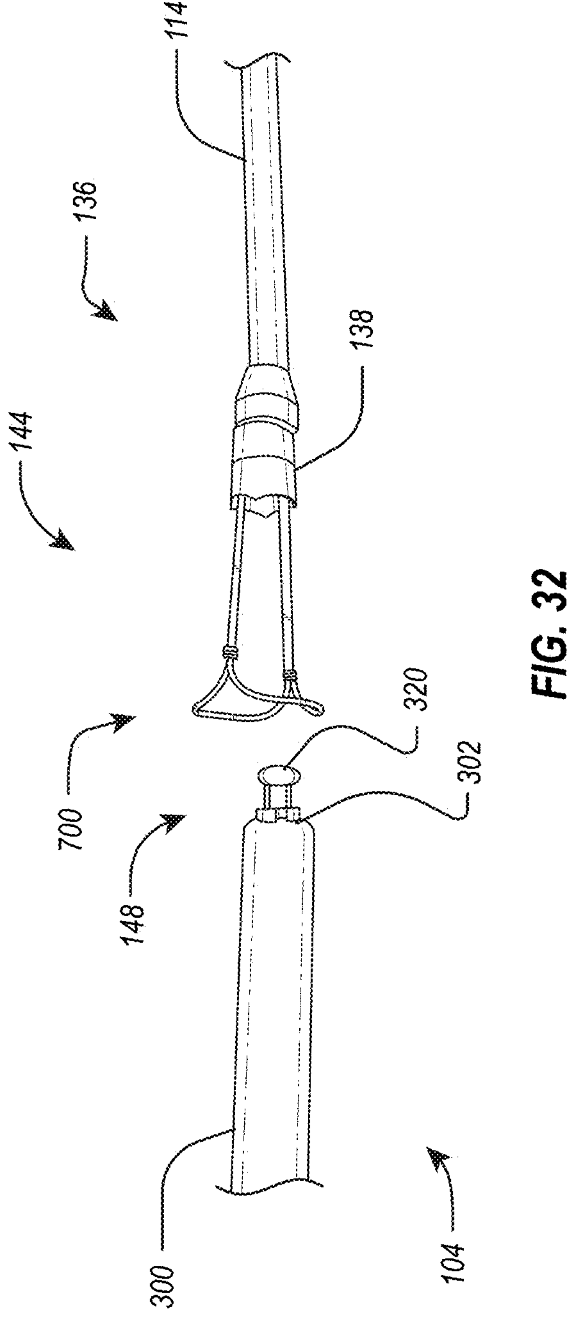
FIG. 32 illustrates an example docking space disposed relative to a docking projection of a leadless pacemaker.

As can be understood from FIGS. 32-36, to engage the docking projection 148 and lock the leadless pacemaker 104 in the docked position with the catheter system 108, the docking space formed by the snare 700 is disposed relative to at least a portion of the docking projection 148, such as the docking button 320, as shown in FIG. 32. The snare 700 is then advanced distally over the leadless pacemaker 104 until the docking projection 148 is disposed in the docking space. For example, the first snare loop and the second snare loop are advanced distally until the docking button 320 is disposed in the docking space of the snare 700, as shown in FIG. 33A. The snare 700 may be advanced by advancing the catheter system 308, the snare 700, and/or the first and second sheaths 702 and 704. The first and second sheaths 702 and 704 are translatable through the docking cap 136, and the first snare wire 714 and the second snare wire 716 are each translatable within the first snare lumen 710 and the second snare lumen 712.

Figures 33A, 33B:
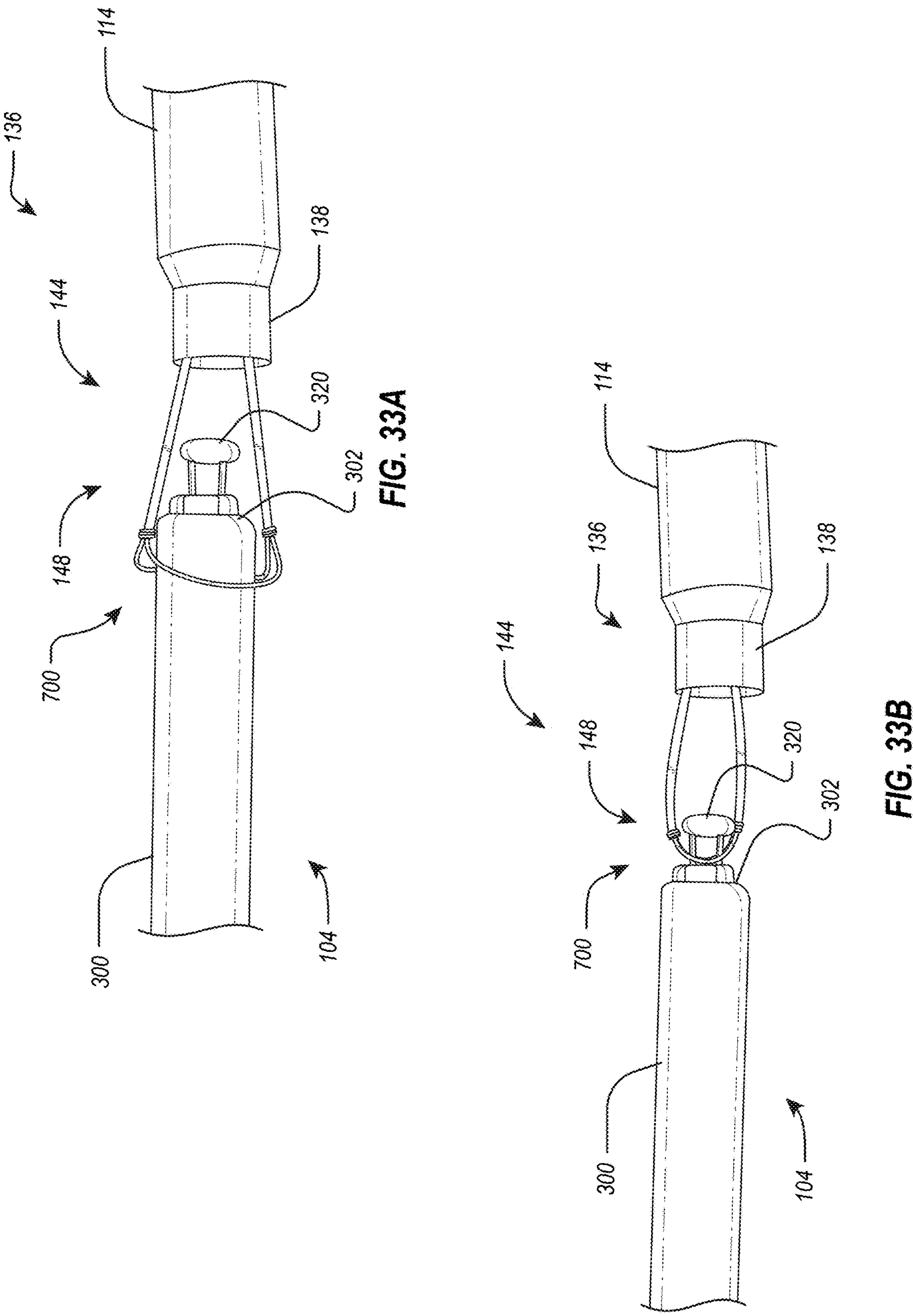
FIG. 33A shows the snare advanced over the leadless pacemaker with the docking projection disposed in the docking space.
FIG. 33B illustrates the snare tightened around the docking projection in an engaged position.
Figure 34:
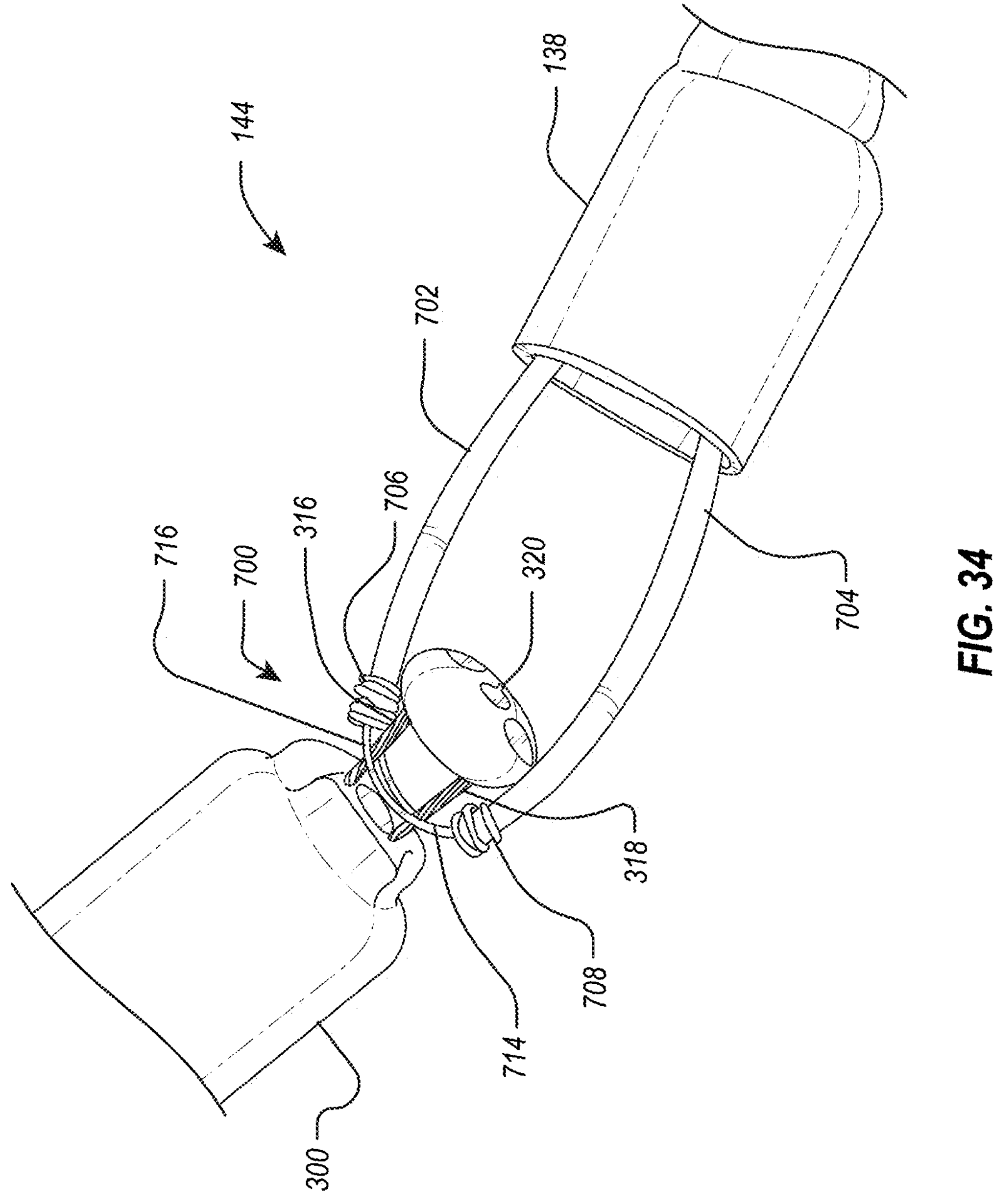
FIG. 34 is a detailed view of the snare tightened around the docking projection in the engaged position.

The snare 700 is moveable from the disengaged position to the engaged position, shown in FIGS. 33B and 34, by translating the first snare wire 714 and the second snare wire 716 proximally within the first snare lumen 710 and the second snare lumen 712. Stated differently, the first and second snare wires 714 and 716 are each retracted into the first and second snare lumens 710 and 712. The proximal translation of the first and second snare wires 714 and 716 tightens the snare 700, closing the first and second snare loops into smaller loops. Stated differently, a peak of each of the snare loops formed by the first snare wire 714 and the second snare wire 716 moves proximally towards a distal end of the first and second sheaths 702 and 704 decreasing a size of each of the snare loops. Additionally, the peaks of the snare loops formed by the first snare wire 714 and the second snare wire 716 simultaneously move towards each other and a central axis of the docking space during the proximal translation of the first and second snare wires 714 and 716. The movement of the peaks radially inwards towards each other and the central axis decreases a size of the docking space and tightens the first and second snare wires 714 and 716 around at least a portion of the docking projection 148, thereby locking the docking projection 148 in the engaged position. For example, as shown in FIGS. 33B and 34, the size of the docking space may be decreased until the first and second wires 714 and 716 close around the first and second posts 316 and 318 and/or the size of the docking space is smaller than a size of the docking button 320.

Figure 35:
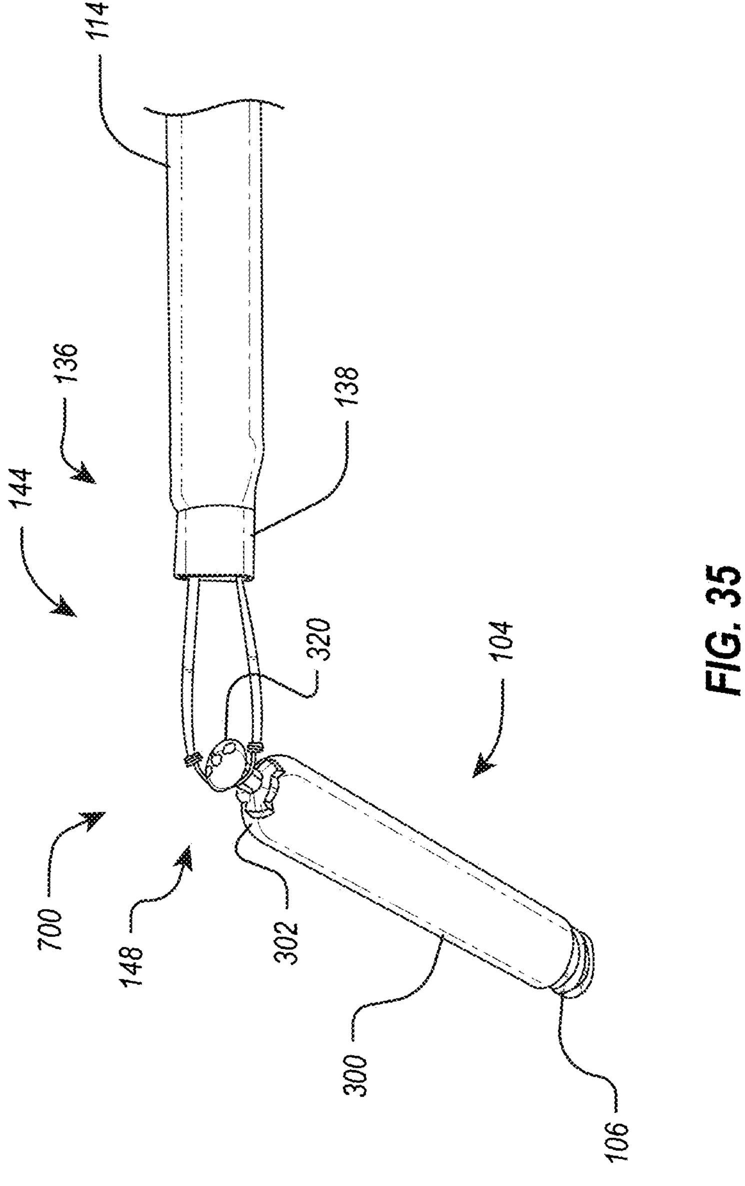
FIG. 35 illustrates movement of the leadless pacemaker relative to a longitudinal axis of the catheter in the engaged position.

The snare 700 captures and locks the docking projection 148 in the engaged position with a freedom of movement of the leadless pacemaker 104. More particularly, as shown in FIG. 35, the engagement of the snare 700 with the docking projection 148 provides a junction that permits movement of the leadless pacemaker 104 relative to a longitudinal axis of extending through the chamber 142 and/or one or more lumens of the catheter system 108. The movement may be parallel or at an angle to the longitudinal axis without releasing the leadless pacemaker 104 from the catheter system 108. For example, as shown in FIG. 35, the junction may act like a hinge allowing the repositioning of the leadless pacemaker 104 without release.

Figure 36:
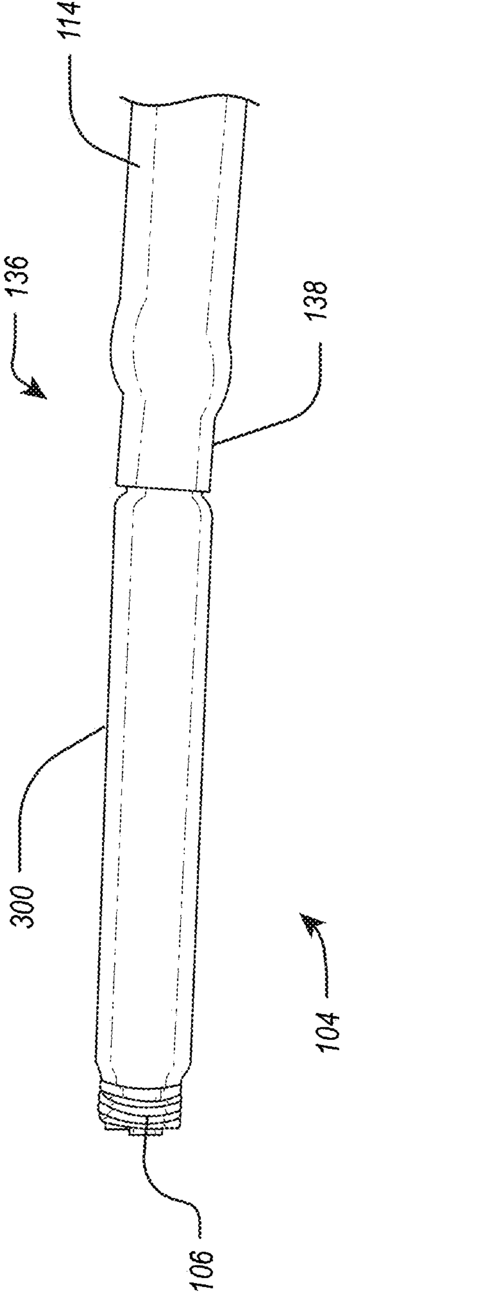
FIG. 36 shows the leadless pacemaker docked to the docking cap.
Figure 37:
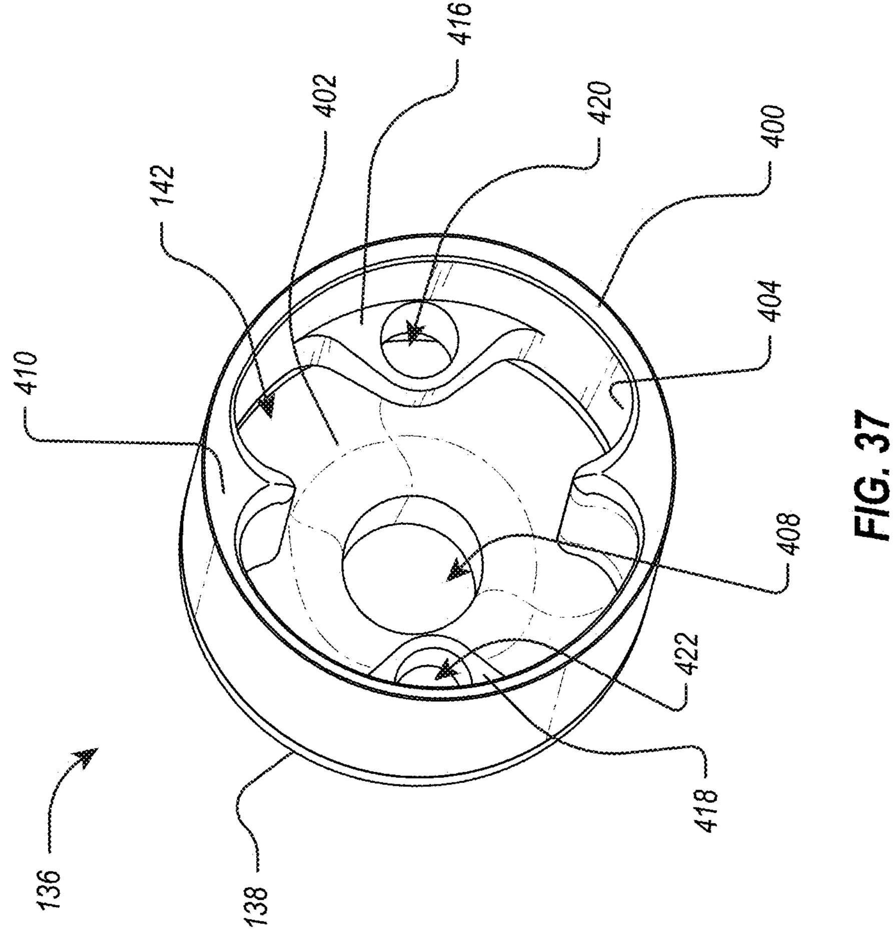
FIG. 37 illustrates an example docking cap having a first tracker and a second tracker.

Once the snare 700 is in the engaged position with the docking projection 148, to move the leadless pacemaker 104 to the docked position with the catheter 108, as shown in FIG. 36, the first sheath 702 and the second sheath 704 are retracted proximally until the docking projection 148 is disposed within the chamber 142 of the docking cap 136. In the docked position, the leadless pacemaker 104 may be moved through the patient anatomy to and/or from the implant site. During retrieval, the snare 700 and/or other features of the retriever 144 may include a cutting edge or similar mechanism for removing tissue overgrowth on the leadless pacemaker 104. Further, the retriever 144 may be used in a tether and/or test mode, for example, to test for thresholds by advancing the first and second sheaths 702 and 704 along with the first and second snare wires 714 and 716, such that the docking projection 148 remains engaged with the snare 700.

For a detailed description of the interaction of the retriever 144 with the docking cap 136, reference is made to FIGS. 37-40. In one implementation, the body 138 of the docking cap 136 includes one or more cap surfaces, as described herein, adapted to provide torque to the leadless pacemaker 104 via the docking surfaces of the docking end of the leadless pacemaker 104. In one implementation, the one or more cap surfaces are disposed relative to the chamber 142 and are adapted to matingly engage the docking surfaces and/or features of the retriever 144. The one or more cap surfaces may include the distal end surface 400, the proximal chamber surface 402, and the side surface 404 extending between the proximal chamber surface 402 and the distal end surface 400. The distal end surface 400 defines an opening into the chamber 132, and the proximal chamber surface 402 defines the proximal opening 408 into the chamber 142 extending through the receiving portion 140. The proximal opening 408 may be coaxial with the longitudinal axis of a lumen of the torque shaft 114 and/or the steerable catheter 118 and the central axis of the snare 700.

The mating engagement of each of the various cap surfaces with the corresponding docking surfaces provides torque transmission. To further facilitate torque transmission, one or more of the cap surfaces may include the cap keys 410. In one implementation, the cap keys 410 are disposed radially around the side surface 404, for example, on radially opposite sides of the longitudinal axis. The cap keys 410 may be adapted to matingly engage corresponding side keys 310 defined in the docking projection 148 for torque transmission, as described herein.

In one implementation, the docking cap 136 further includes one or more trackers corresponding to the one or more sheaths of the retriever 144. For example, the docking cap 136 may include a first tracker 416 corresponding to the first sheath 702 and a second tracker 418 corresponding to the second sheath 704. In one implementation, the first and second trackers 416 and 418 maintain the first and second sheaths 702 and 704 in an orientation relative to each other and to the center axis coaxial with the longitudinal axis running through the proximal opening 408. The orientation may include, for example, the first sheath 702 maintained in a position radially opposite the second sheath 704 about the center axis. Stated differently, the first and second sheaths 702 and 704 may be disposed approximately 180 degrees apart about the center axis.

Figure 38:
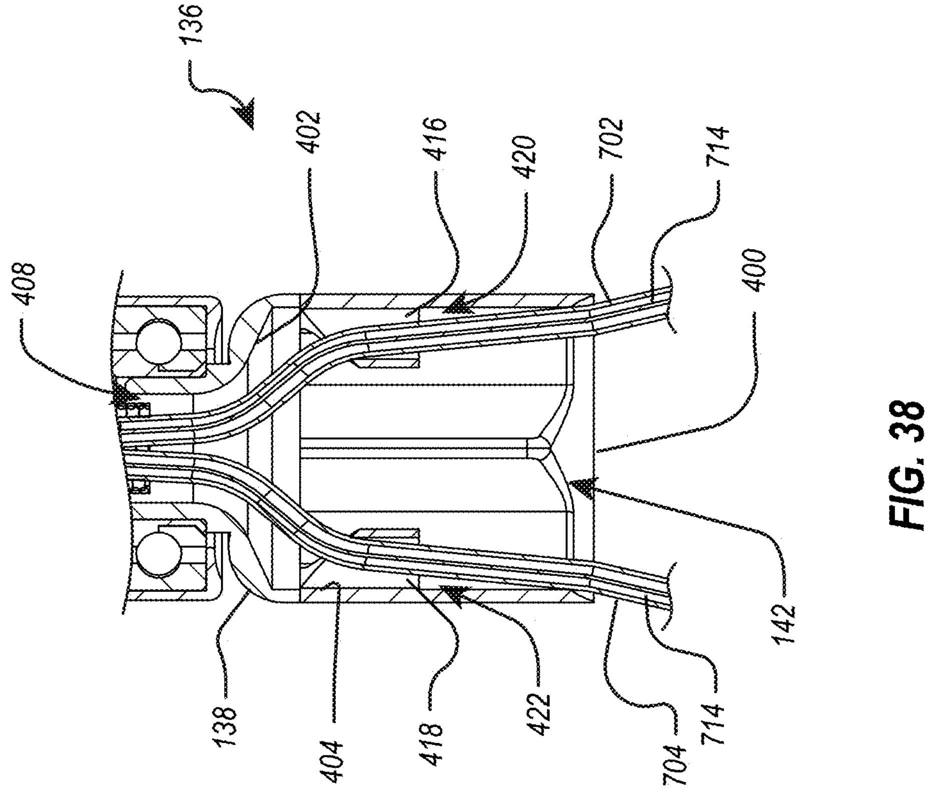
FIG. 38 is a cross-section of a retriever in the form of a snare disposed in a chamber of a docking cap.
Figure 39:
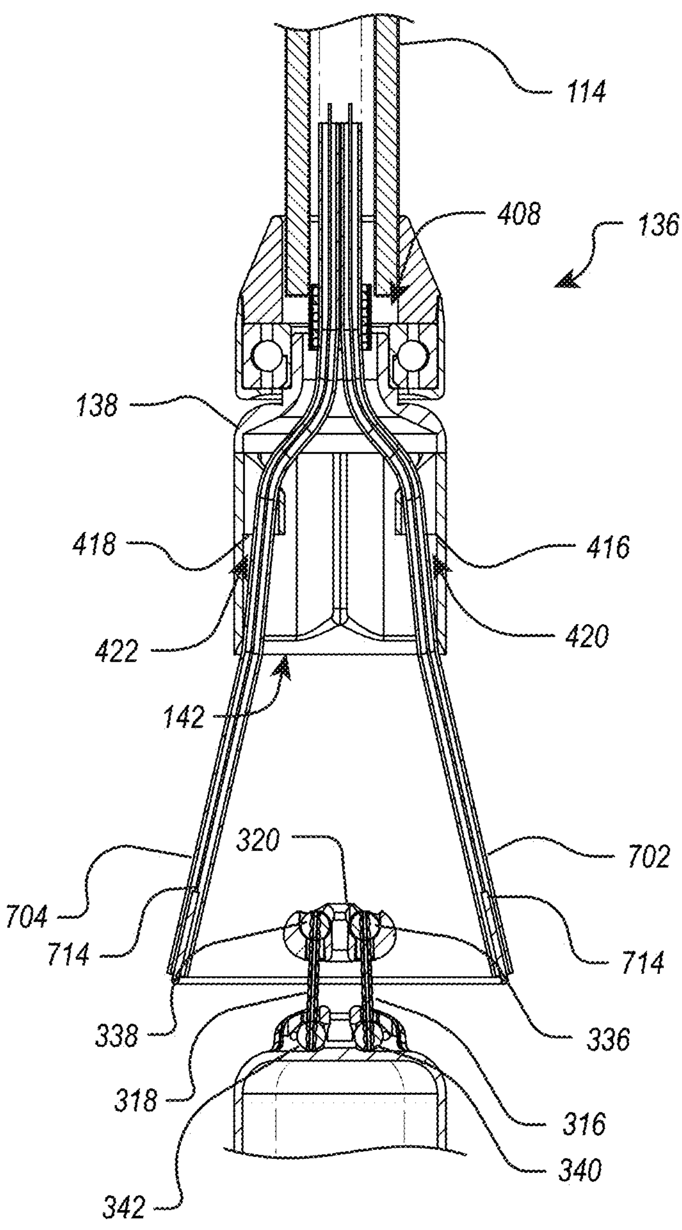
FIGS. 39 and 40 are each a cross-section of a distal end of a catheter system showing a snare engaged to a docking projection of a leadless pacemaker.
Figure 40:
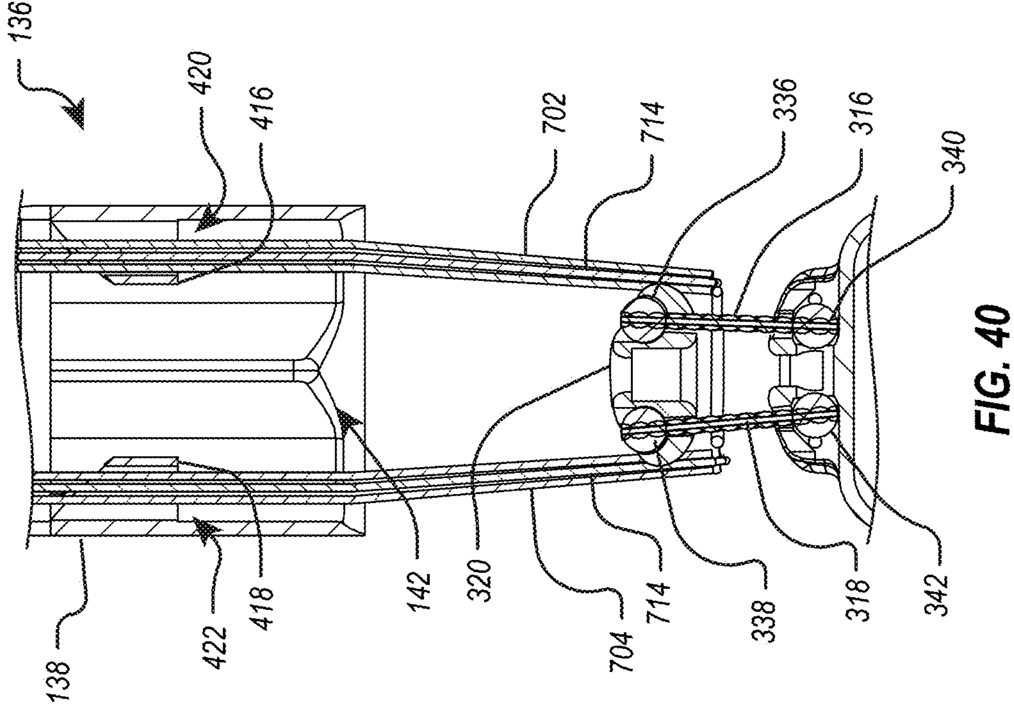

The first and second sheaths 702 and 704 are translatable within the first and second trackers 416 and 418, respectively. In one implementation, the first tracker 416 includes a first tracker lumen 420 within which the first sheath 702 is translatable, and the second tracker 418 includes a second tracker lumen 422 within which the second sheath 704 is translatable, as shown in FIGS. 38-40. The first and second trackers 416 and 418 thus maintain the first and second sheaths 702 and 704 in an orientation adapted to position the snare 700 for capturing the docking projection 148 such that it can be moved into the chamber 142 into the docking position by retracting the first and second sheaths 702 and 704 into the lumen of the torque shaft 114.

In one implementation, the docking button 320 is mounted to the docking projection 148 with a set of docking balls fixed to the first and second posts 316 and 318, as shown in FIGS. 39-40. The first post 316 may extend between a first proximal ball 336 and a first distal ball 340. The first proximal ball 336 is disposed in the first slot 328, and the first distal ball 340 extends through an opening in the end surface 308, thereby mounting the docking button 320 to the docking projection 148 with the first post 316.

Similarly, the second post 318 may extend between a second proximal ball 338 and a second distal ball 342. The second proximal ball 338 is disposed in the second slot 330, and the second distal ball 342 extends through another opening in the end surface 308, thereby mounting the docking button 320 to the docking projection 148 with the second post 318. In one implementation, the first post 316 is mounted to the docking projection 148 and the docking button 320 such that it is radially symmetric with the second post 318.

It will be appreciated that the retriever 144 may be displaced to engage the docking projection 148 using the docking cap 136 as described herein. Additionally or alternatively, a push-pull actuator 826 may be used to cause the retriever 144 to engage and disengage the docking projection 148. For example, turning to FIGS. 41-46, in one implementation, the retriever 144 is in the form of a hinged grasper and displaceable between the engaged and disengaged position with a push-pull actuator 826.

Figure 41:
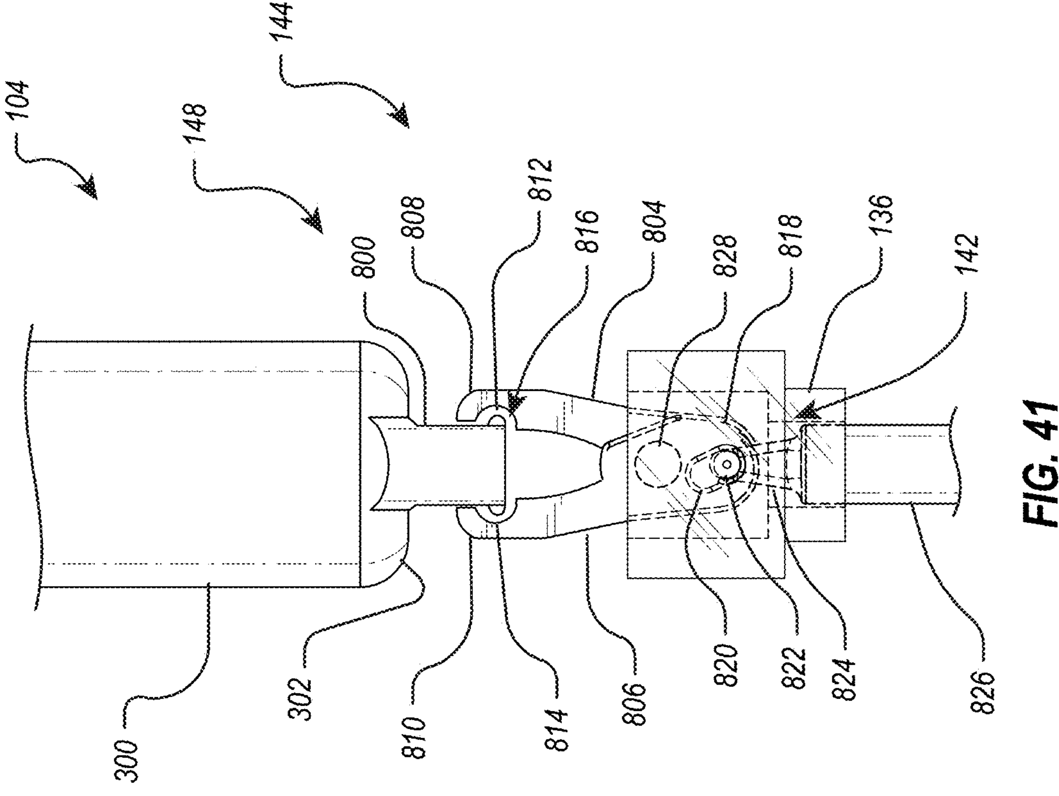
FIG. 41 shows a front view of the retriever in the form of a hinged grasper engaged to a slotted docking projection of a leadless pacemaker and displaceable with a push-pull actuator, with a docking cap shown transparent.
Figure 42:
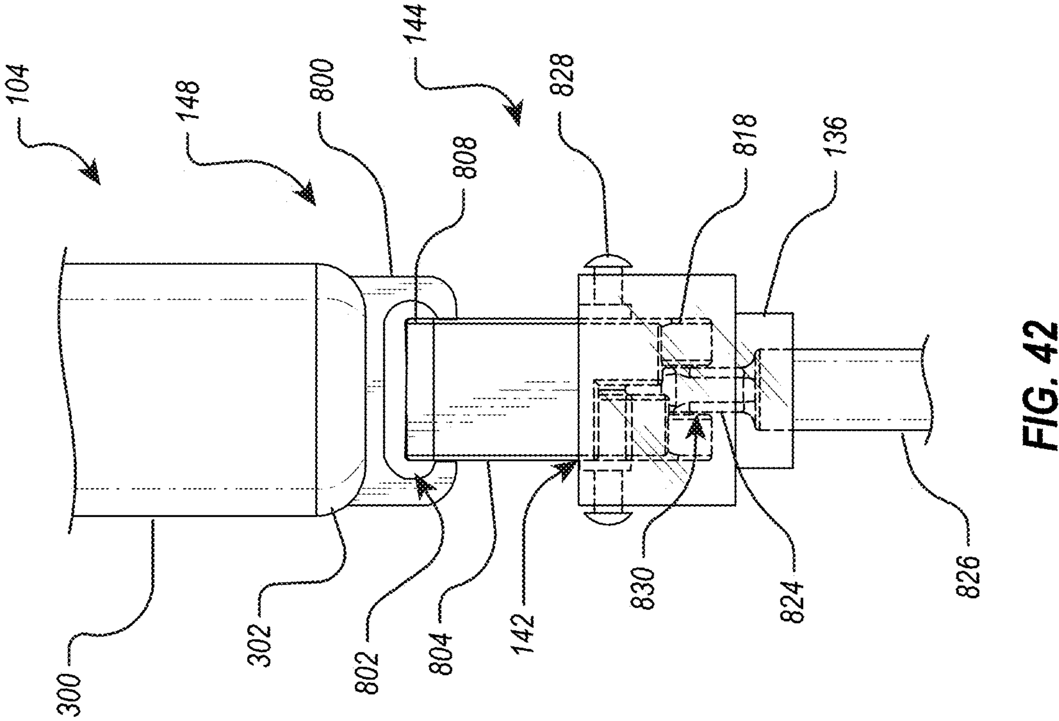
FIG. 42 shows a side view of the hinged grasper of FIG. 41.
Figure 43:
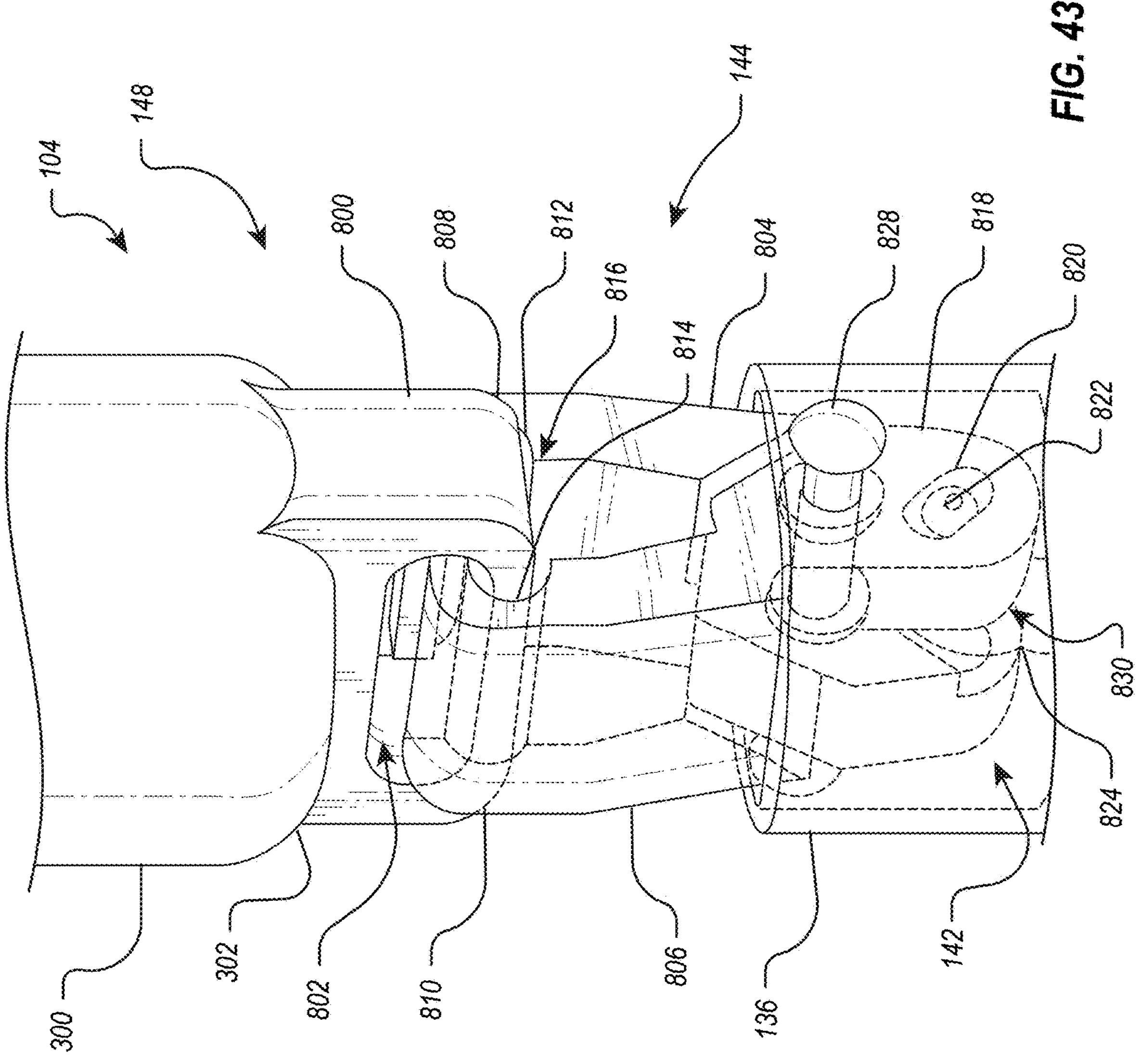
FIG. 43 is a detailed perspective view of the hinged grasper of FIG. 41 shown with the arms of the hinged grasper also transparent.

Referring first to FIGS. 41-43, in one implementation, the leadless pacemaker 104 includes the docking projection 148 extending from the surface 302 at the docking end of the body 300. The docking projection 148 includes a projection 800 defining a slot 802. In one implementation, the projection 800 has a length extending in a first direction across the surface 302, such that the length is approximately the same as a diameter of the surface 302, and the projection 800 has a narrow width extending in a second direction across the surface 302, with the width being less than the diameter of the surface 302.

The projection 800 includes one or more docking surfaces defining the slot 802 and configured to matingly engage corresponding features of the retriever 144, thereby providing torque transmission to the leadless pacemaker 104. In one implementation, the retriever 144 in the form a hinged grasper is formed with a first arm 804 and a second arm 806. A first grasping portion 808 is disposed at a distal end of the first arm 804 and includes a first cutout 812. Similarly, a second grasping portion 810 is disposed at a distal end of the second arm 806 and includes a second cutout 814.

The first cutout 812 and the second cutout 814 collectively define a docking space 816 adapted to engage the projection 800. More specifically, to engage the leadless pacemaker 104 in the engaged position, lips of the grasping portions 808 and 810 extend into the slot 802 with a proximal portion of the projection 800 disposed in the docking space 816, thereby gripping the docking projection 148 with the retriever 144. The first arm 804 and the second arm 806 move radially outwardly into the disengaged position and the grasping portions 808 and 810 release the projection 800, widening the docking space 816. In one implementation, the first arm 804 and the second arm 806 each taper in width proximally from the grasping portions 808 and 810 to a base 818.

To move the arms 804 and 806 between the engaged and disengaged positions, the push-pull 826 actuator is translated relative to the docking cap 136 within the chamber 142. The push-pull actuator 826 may extend through and be translated within a lumen of the torque shaft 114. In one implementation, the push-pull actuator 826 includes a neck 824 extending distally from a body of the push-pull actuator 826. The neck 824 includes one or more knobs 822 extending radially outwardly from a longitudinal axis of the push-pull actuator 826. The neck 824 is disposed within a gap 824 defined in each of the first arm 804 and the second arm 806, and each of the knobs engage corresponding tracks 820 in each of the arms 804 and 806. One or more hinge pins 828 extend through holes in the docking cap 136 and the arms 804 and 806 to rotationally mount the retriever 144 to the docking cap 136. Engagement of the knobs 822 with the arms 804 and 806 within the tracks 820 causes the push-pull actuator 826 to displace the arms 804 and 806 radially inwardly and outwardly relative to a rotational axis of the hinge pin(s) 828 when the body of the push-pull actuator 826 is translated distally and proximally.

Figure 44:
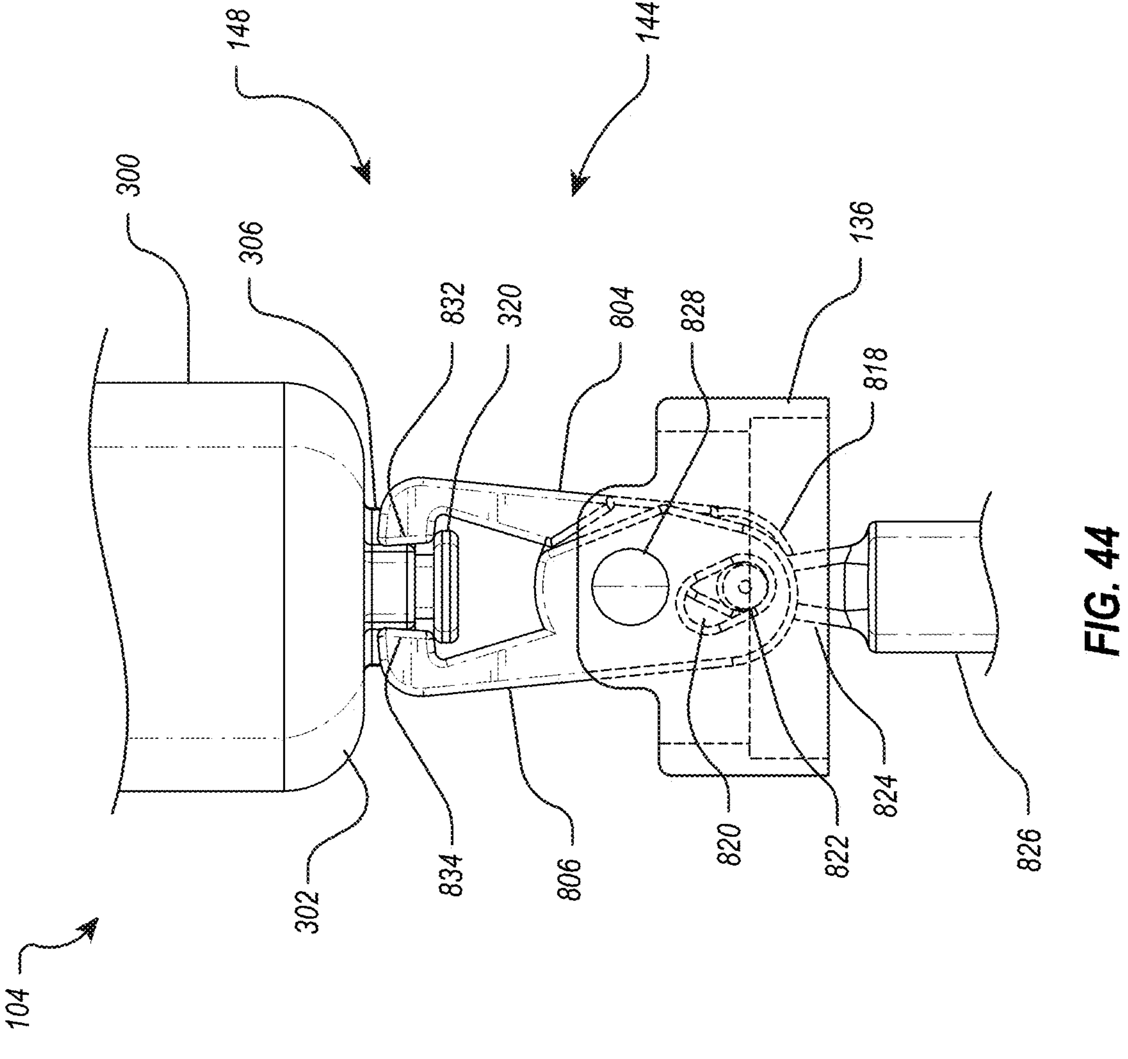
FIG. 44 shows a front view of the retriever in the form of another hinged grasper engaged to a polygonal docking projection of a leadless pacemaker and displaceable with a push-pull actuator, with a docking cap shown transparent.
Figure 45:
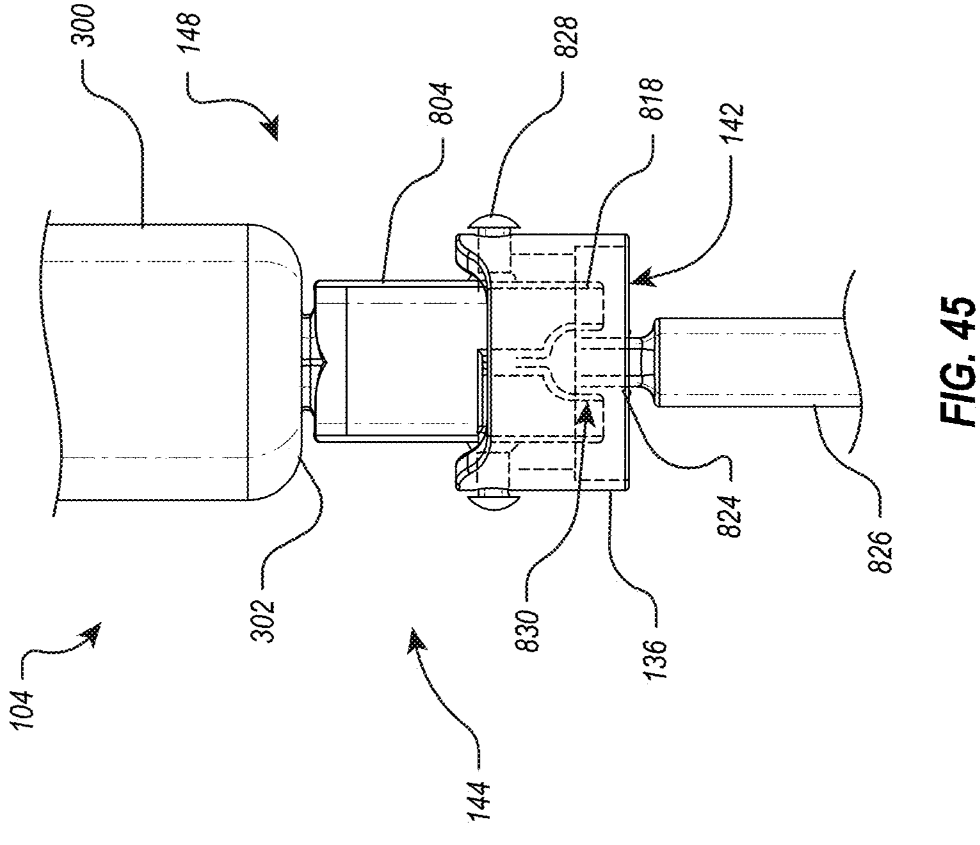
FIG. 45 shows a side view of the hinged grasper of FIG. 44.
Figure 46:
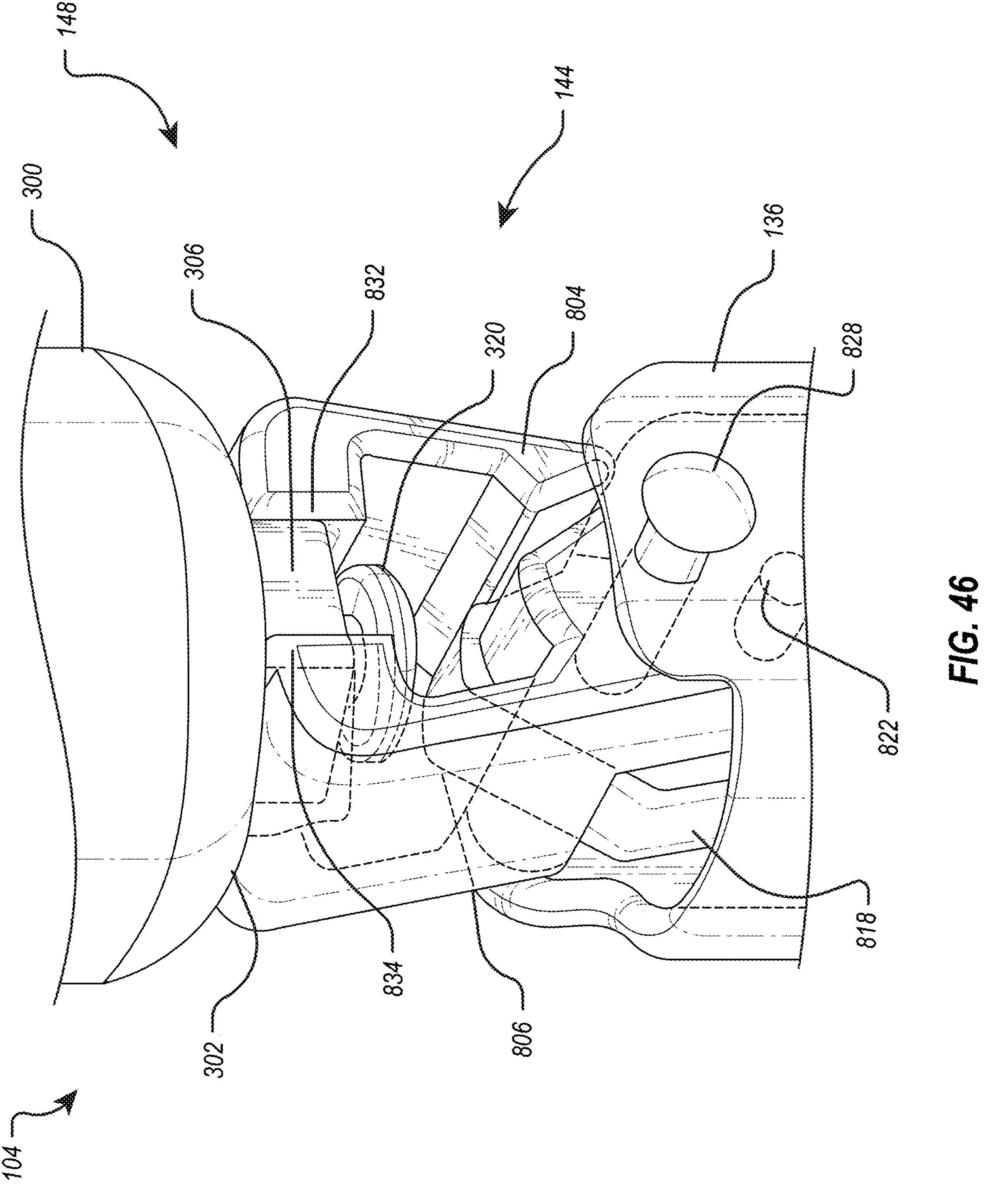
FIG. 46 is a detailed perspective view of the hinged grasper of FIG. 44 shown with the arms of the hinged grasper also transparent.

Similarly, turning to FIGS. 44-46, the first arm 804 and the second arm 806 are displaceable between the engaged and disengaged position with the push-pull actuator 826. In one implementation, the docking projection 148 includes one or more docking surfaces, including edge docking surfaces 306 and/or the like, configured to matingly engage corresponding features of the first arm 804 and the second arm 806, thereby providing torque transmission to the leadless pacemaker 104. The docking surfaces 306 may form a hexagonal shape or other polygonal shape of the docking projection 148. The first arm 804 may include a first docking surface 832, and the second arm 806 may include a second docking surface 834. Each of the first and second docking surfaces 832 and 834 may be planar or other shapes mirroring a shape of the edge docking surfaces 306.

The first docking surface 832 and the second docking surface 834 are adapted to engage one or more of the edge docking surfaces 306 of the docking projection 148. More specifically, to engage the leadless pacemaker 104 in the engaged position, first docking surface 832 and the second docking surface 834 are pressed against the edge docking surfaces 306, thereby gripping the docking projection 148 with the retriever 144. The first arm 804 and the second arm 806 move radially outwardly into the disengaged position and the grasping portions 808 and 810 release the docking projection 148.

The foregoing merely illustrates the principles of the presently disclosed technology. Various modifications and alterations to the described implementations will be apparent to those skilled in the art in view of the teachings herein. It will thus be appreciated that those skilled in the art will be able to devise numerous systems, arrangements and methods which, although not explicitly shown or described herein, embody the principles of the presently disclosed technology and are thus within the spirit and scope of the present presently disclosed technology. From the above description and drawings, it will be understood by those of ordinary skill in the art that the particular implementations shown and described are for purposes of illustrations only and are not intended to limit the scope of the present presently disclosed technology. References to details of particular implementations are not intended to limit the scope of the presently disclosed technology.

What is claimed is:

1. A biostimulator, comprising:

a body having a fixing end and a docking end on a longitudinal axis;

a helical anchor at the fixing end to attach to tissue; and a docking projection extending in a proximal direction from the docking end and having three or more side keys notched in an end surface, wherein a depth of each side key decreases in the proximal direction.

2. The biostimulator of claim 1, wherein the end surface has a curved profile, and wherein each side key extends over the curved profile.

3. The biostimulator of claim 1, wherein a circumferential distance between the side keys decreases in the proximal direction.

4. The biostimulator of claim 1, wherein a width of each side key varies in the proximal direction.

5. The biostimulator of claim 1, wherein the three or more side keys are rotationally symmetric about the longitudinal axis.

6. The biostimulator of claim 1, wherein the three or more side keys include dimples in the end surface.

7. The biostimulator of claim 1, wherein the docking projection includes a neck radially inward from the end surface.

8. A catheter system, comprising:

a torque shaft having a longitudinal axis; and a docking cap coupled to the torque shaft, wherein the docking cap has a cap surface defining a chamber to receive a docking projection, and wherein the docking cap includes three or more cap keys extending over the cap surface, wherein a height of each cap key decreases in a proximal direction.

9. The catheter system of claim 8, wherein the cap surface has a curved profile.

10. The catheter system of claim 8, wherein the three or more cap keys are rotationally symmetric about the longitudinal axis.

11. A biostimulator system, comprising:

a biostimulator including a body having a fixing end and a docking end on a longitudinal axis, a helical anchor at the fixing end to attach to tissue, and a docking projection extending in a proximal direction from the docking end and having three or more side keys notched in an end surface, wherein a depth of each side key decreases in the proximal direction; and a catheter system including a torque shaft extending along the longitudinal axis, and a docking cap coupled to the torque shaft, wherein the docking cap has a cap surface defining a chamber to receive the docking projection, and wherein the docking cap includes three or more cap keys extending over the cap surface.

12. The biostimulator system of claim 11, wherein the end surface has a curved profile, and wherein each side key extends over the curved profile.

13. The biostimulator system of claim 11, wherein a circumferential distance between the side keys decreases in the proximal direction.

14. The biostimulator system of claim 11, wherein a width of each side key varies in the proximal direction.

15. The biostimulator system of claim 11, wherein the three or more side keys are rotationally symmetric about the longitudinal axis.

16. The biostimulator system of claim 11, wherein the three or more side keys include dimples in the end surface.

17. The biostimulator system of claim 11, wherein the cap surface has a curved profile.

18. The biostimulator system of claim 11, wherein the three or more cap keys are rotationally symmetric about the longitudinal axis.

* * * * *